(12) United States Patent
Yaguchi et al.

(10) Patent No.: US 6,992,286 B2
(45) Date of Patent: Jan. 31, 2006

(54) MATERIAL CHARACTERIZATION SYSTEM

(75) Inventors: Toshie Yaguchi, Higashiibaraki (JP); Takeo Kamino, Hitachinaka (JP); Yoshifumi Taniguchi, Hitachinaka (JP)

(73) Assignees: Hitachi High-Technologies Corporation, Tokyo (JP); Hitachi-Science Systems, Ltd., Ibaraki (JP)

(*) Notice: Subject to any disclaimer, the term of this patent is extended or adjusted under 35 U.S.C. 154(b) by 0 days.

(21) Appl. No.: 10/792,781

(22) Filed: Mar. 5, 2004

(65) Prior Publication Data
US 2004/0183012 A1 Sep. 23, 2004

(30) Foreign Application Priority Data
Mar. 18, 2003 (JP) .................................. 2003-073932

(51) Int. Cl.
  *G01N 23/203* (2006.01)

(52) U.S. Cl. ........................ 250/306; 250/311
(58) Field of Classification Search ................ 250/306, 250/307, 311, 310
See application file for complete search history.

(56) References Cited

U.S. PATENT DOCUMENTS 5,557,104 A * 9/1996 Field et al. ................ 250/307

FOREIGN PATENT DOCUMENTS

| JP | 59-163550 | 9/1984 |
| JP | 01-209648 | 8/1989 |
| WO | WO 02/068944 | 9/2002 |

* cited by examiner

*Primary Examiner*—Kiet T. Nguyen
(74) *Attorney, Agent, or Firm*—Dickstein Shapiro Morin & Oshinsky LLP

(57) ABSTRACT

An electron beam device is provided with an electron beam diffraction image analysis section for calculation of the lattice distance from the diffraction image taken into by the TV camera for observation of the electron beam diffraction image, the EDX analysis section for acquiring a composition of the material, the data base for retrieval of material characterization, and the material characterization section having the data base retrieval function. The material characterization section characterizes the material by retrieving the retrieval data base, based upon the lattice distance data transferred from the electron beam diffraction image analysis section and the element data transferred from the EDX analysis sectio.

13 Claims, 20 Drawing Sheets

$-\phi$ $-\phi$

FIG. 19

51 — LATTICE DISTANCE DATA
- d1 = 0.123
- d2 = 0.101
- ⋮

52 — COMPOSITION DATA
- A
- B
- C

| MATERIAL | | $ABC_3$ | $AB_2C_3$ | .... | .... | .... |
|---|---|---|---|---|---|---|
| COMPOSITION | | ABC | ABC | ABC | ABC | .... |
| LATTICE DISTANCE | d1 | 0.141 | 0.123 | 0.222 | 0.123 | .... |
| | d2 | 0.101 | 0.101 | 0.200 | 0.111 | .... |
| | d3 | ⋮ | ⋮ | ⋮ | ⋮ | |
| | d4 | | | | | |

(54 indicates $AB_2C_3$ column; 53 indicates the next column)

| DATA NO. | 1 |
|---|---|
| SPECIMEN IMAGE | 1-IMAGE |
| DIFFRACTION IMAGE | 1-DEFF |
| EDX SPECTRUM | 1-EDX |
| LATTICE DISTANCE DATA | d1 = 0.123<br>d2 = 0.101<br>.... |
| COMPOSITION DATA | A, B, C |
| RESULT OF RETRIEVAL | $AB_2C_3$ |

MATERIAL CHARACTERIZATION SYSTEM

CROSS REFERENCE OF RELATED APPLICATION

This application claims the priority of Japanese patent Application No. 2003-073932, filed Mar. 18, 2003 under the Paris convention.

FIELD OF THE INVENTION

The present invention relates to a material characterization system for characterizing substances in a material by a combination of electron beam diffraction image and energy analysis result.

RELATED ART

In characterization of a substance using an electron device such as electron microscopes, a transmission image of a specimen is observed and recorded, at first. Then, the observed and recorded electron diffraction image is subjected to measurement of the distance between recorded diffracted beam spots so as to acquire the lattice distance. In this case, there may be fluctuation in measured values, because an operator decides a point the operator thinks it as the center of the spot.

In order to increase the accuracy, it is necessary to measure plural spots for each of the spots, and to calculate the lattice distance with respect to each of the set of the spots. Further, the electron microscope is converted to an EDX (energy dispersive X-ray spectroscopy) mode; the focused electron beam is irradiated to the specimen; then constituting elements are detected from the characterization X-ray emitted irradiated region of the specimen. At the same time, X-ray emitted from structure components near the specimen other than the specimen is detected. The operator removes elements of the structure components other than the specimen, based on experience to select the elements of the specimen.

Then, the operator identifies a possible substance consisting of the detected elements by reference to the data base of the lattice distances that are measured by X-ray diffraction. In transmission electron-microscopes, in general, all these operations are carried out independently by manual; then the operator synthesizes the respective results to identify a substance. Further, the operator analyzes and arranges diffraction images corresponding to transmitted images and EDX analytical results, based on the transmitted images, electron beam diffraction images, EDX analytical results, etc.

In the patent publication 1, there is disclosed a method of identification wherein a strength of each of the pixels to which the diffraction images are projected; and a set of d values of the substance is acquired based on the distance from a coordinate of a pixel as the main spot whose strength is maximum to coordinates of the pixels to which other diffraction spots are projected.

Patent Publication 1: Japanese Patent Publication hei 04-11822 (1992)

In the above-mentioned related art, however, all works of acquisition of data through identification of the substance are carried out by manual, which requires one or two days and a lot of jobs. In EDX analysis, candidates of elements corresponding to each of the peaks are listed by automatic identification. However, such elements as corresponding to system X-ray emitted from irradiation system lens of the electron microscope that is essentially not contained in the analytical zone or corresponding to stray light X-ray emitted from a region of a specimen other than the irradiated region may be listed. Judgment whether the elements are in the analytical zone or not requires experience of the operator.

Further, since the directions of scanning transmitted images and diffraction images are not always in coincidence, it was necessary to observe a lattice structure with a high magnitude image and to make the sights of the diffraction image and lattice image are in coincidence.

In the method disclosed in the patent document 1, since the main spot has a very high strength, so that brightness has a spread area to occupy several pixels at the maximum strength, it is difficult to decide the center accurately. Further, since the strength distribution by setting coordinates of all areas of acquired electron beam diffraction images is calculated, it will take a long time to acquire the lattice distance.

BRIEF DESCRIPTION OF THE DRAWINGS

FIG. 19 is an example of data stored in the material characterization section.

SUMMARY OF THE INVENTION

Figure 1:
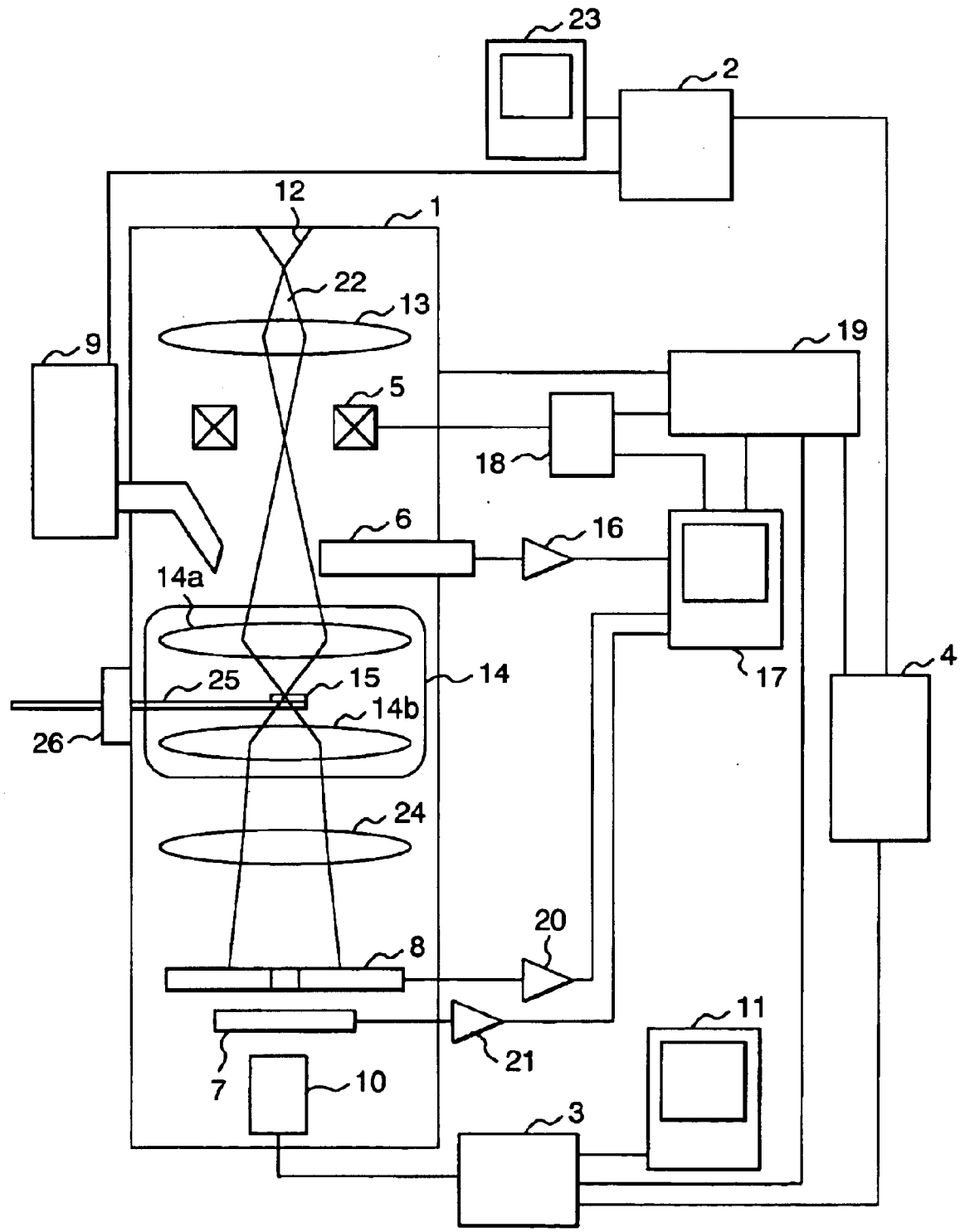
FIG. 1 is a diagrammatic Drawing of the material characterization system according to the present invention.

The present invention aims at a great reduction of an amount of manual work done by an operator, and it is possible to carry out the characterization with high efficiency.

DETAILED DESCRIPTION OF THE INVENTION

A material characterization system according to one aspect of the present invention comprises:

means for irradiating a specimen with an electron-beam by stopping down an electron gun; an electron-beam scanning section for scanning the specimen with the electron-beam;

an electron detector for detecting secondary electrons emitted from the specimen upon irradiation of electron-beam or electrons transmitted through the specimen;

a specimen image display section; an elemental analysis section for analyzing an energy beam emitted by synergetic action between the electron-beam and the specimen;

an electron-beam diffraction image photography section for picking up an electron diffraction image formed by the specimen transmission electron-beam;

an electron-beam diffraction image analysis section for outputting information of the specimen concerning a lattice distance of a crystal obtained from the electron diffraction image; and a material characterization section for identifying the material contained in an area of electron irradiation zone of the specimen. When the system according to the present invention is used, identification of material in a specific area of a specimen can be carried out rapidly, easily and at high accuracy.

The elemental analysis section can be an energy disperse X-ray analysis section for outputting element information by analyzing characterization X-ray emitted from the specimen upon electron irradiation. In this case, the system is preferably provided with an elemental analysis section, which has a judging section for judging whether to output the elemental information based on the ratio of the strength of Ka ray of characterization X-ray spectrum of each element to the strength of La ray.

By this judging section, it is possible to specify the specimen material based on the composition information and lattice distance data of a crystal by reference to data base of lattice distance of crystals of various materials, after elements other than ones present in the analytical object region are removed from the elements detected by EDX analysis.

The elemental analysis section can be an electron energy loss spectroscopy section for outputting elemental information by analyzing energy loss spectrum of a specimen transmission electron-beam. In the material characterization system according to the present invention, a scanning image, elemental information, an electron-beam diffraction image and information concerning an identified material are stored as a set of information, all of the above information having been acquired by analysis of one point of the specimen.

Another aspect of the material characterization system according to the present invention further comprises:

an electron-beam diffraction image display section for display an electron-beam diffraction image photographed with the electron-beam diffraction image photography section; a camera length adjusting lens of an electron-beam diffraction image camera; and a control section for controlling the electron-beam scanning section, wherein the control section controls the electron-beam scanning section so as to rotate the image displayed on the specimen image display section by the same angle as the rotation angle of the specimen image, the rotation angle being caused by changing of the setting of the camera length adjusting lens.

According to the construction, the direction of the scanning image of the specimen and the direction of the electron beam diffraction image of the scanning region can be always in coincidence so tat the image interpretation such as degree of orientation, etc can be easily conducted. Instead of the control section for controlling the electron beam scanning section, the material characterization system further comprises a control section for controlling the electron beam diffraction image display section, whereby the control section controls images displayed on the electron beam diffraction display section by rotating in the reverse direction the images displayed on the electron beam diffraction display section, the angle of the rotation being the same as that of the rotation of the electron beam diffraction image, which is formed by changing of the camera length control lens.

According to this construction, the directions of the scanning image of a specimen and of the electron beam diffraction image of the region are always in coincidence so that image interpretation such as degree of orientation, etc. can be easily conducted.

The electron-beam image analysis section can comprise: means for making a short axis strength profile accumulating pixel strength in the lengthwise direction in each of the short lengths of a squares region set so as to embrace the main spot and at least two spots which are set for the electron-beam diffraction image of a spot form displayed on the electron-beam diffraction display section;

means for making a long axis strength profile accumulating pixel strength in the short length direction in each of the lengthwise sides of the square region;

means for rotating the square region around the center thereof; and means for calculating the lattice distance of a crystal from a distance between peaks of the profiles measured at rotating positions of the square region where the profile in the short length direction is the maximum. The spot embraced by the square region is two spots comprising the main spot and one spot adjoining thereto, or three spots comprising the main spot and two spots symmetric to the main spot.

Further, the electron-beam diffraction analysis section can be composed of:

means for making a short length profile accumulating pixel strength in a lengthwise direction in each of the short lengths of a squares region set so embrace at least two spots which are set for the electron-beam diffraction image of spot form displayed on the electron-beam diffraction display section;

means for making a long axis strength profile accumulating pixel strength in the short length direction in each of the lengthwise sides of the square region; and means for calculating the lattice distance of a crystal based on a distance between the two spots, the distance being calculated from the peak position of the short axis strength profile and the peak position of the long axis peak profile.

The spots embraced by the square region comprise the main spot and one spot adjoining to thereto, for example.

The electron-beam diffraction image analysis section can comprise:

means for acquiring a pixel distribution strength at each of first and second regions which are so set as to embrace two spots of spot like electron-beam images displayed on the electron-beam diffraction display section; and means for calculating a lattice distance based on the distance between the spots acquired by calculated from the peak positions of each of the pixel strength distributions. In this case, the first region and second region embracing the two spots circular of square regions, for example.

The electron-beam image analysis section may comprise:

means for acquiring pixel strength distributions in a region so set as to embrace a main spot displayed on the electron-beam diffraction image display section with respect to the electron-beam diffraction image of a concentric circle where the main spot is the center;

means for acquiring a peak position of the pixel strength distribution;

means for acquiring a strength profile on the straight line intersecting the concentric circle via the peak position;

means for acquiring the peak position of the strength profile; and means for calculating the lattice distance of a crystal based on the peak distance on the straight line. The peak of the strength profile is preferably acquired by fitting the strength profile to a normal distribution or a parabola.

The material characterization system according to the present invention comprises:

means for irradiating a specimen with an electron-beam by stopping down the electron-beam;

an X-ray detector for detecting characterization X-ray emitted from the specimen irradiated with the electron-beam;

an energy dispersive X-ray analysis section for outputting elemental information by analyzing the characterization X-ray detected by the X-ray detector; and a judging section for judging whether the characterization X-ray stems from the element present in the irradiated region or not, based on the strength ratio ($I_L/I_K$) of the Ka and La lines of characterization X-ray identified as ones of an element by the energy dispersive X-ray analysis section.

DETAILED DESCRIPTION OF THE EMBODIMENTS

In the following, the embodiments of the present invention will be explained in detail by reference to the drawings. FIG. 1 is a diagrammatic construction figure of the material characterization system according to the present invention.

In the drawings, the reference numerals are as follows: 1 is an electron beam device, 2.EDX analysis section, 3 an electron beam diffraction analysis section, 4.a material characterization section, 5 a scanning coil, 6 a secondary electron detector, 7 a bright-field scanning transmission electron microscope detector, 8 a dark field scanning transmission electron microscope detector, 9 a EDX detector, 10 a TV camera for observation of electron beam diffraction image, 11 a monitor for observation of the electron beam diffraction image, 12 an electron gun, 13 a condenser lens, 14 an objective lens, 15 a specimen, 16 a signal amplifier, 17 a scanning image display section, 18 a scanning power source, 19 an electron beam device control section, 20 an signal amplifier, 21 a signal display section, 22 an electron gun, 23 a display section, 24 a project lens, 25 a specimen holder, 26 a specimen fine adjuster, 27 a main spot, 28 a diffraction spot, 29 an EELS spectrometer, 30 an EELS analysis section.

The material characterization system comprises an electron beam device 1, EDX analysis section 2, an electron beam diffraction image analysis section 3, a retrieval data base (refer to FIG. 19) for characterization of a material, and a material characterization section 4 having a data base retrieval function. The electron beam device 1 comprises an electron beam gun 12, a condenser lens 13, an object lens 14, and a projection lens 24. A scanning coil 5 is disposed between the condenser lens 13 and the objective lens 14, wherein the scanning coil is supplied with current from a scanning power source 18 under control by an electron beam device controller 19.

The objective lens 14 has a function of two lenses as a pre-magnetic field 14a and post-magnetic field 14b under strong excitation. A specimen 15 supported by a sample holder, which is movable by a specimen goriometer 26 is inserted between the pre-magnetic field 14a and the post-magnetic field 14b. A secondary electron detector 6 is disposed above the specimen 15 and below the scanning coil 5.

An annular detector 8 for observing a dark-field STEM image is disposed below the projector lens 24, and a detector for observing bright-field STEM image is so installed bellow the annular detector 8 as to take-in and take out from an optic axis. Scanning signals are input into a scanning image display 17 from the scanning power source 18.

The electron beam 22 is focused in the form of a spot on the specimen 15 by the condenser lens 13 and the pre-magnetic field 14a of the objective lens 14, and it scan on the specimen 15. The secondary electron detector 6 detects secondary electron emitted from the specimen 15 upon irradiation of the electron beam 22. The bright-field STEM image observing detector 7 detects transmission electron scattered within a half angle detector, i.e. about 50 mrad from the specimen 15. The annular detector 8 detects electron (elastic scattered electron) scattered within a semi angle, i.e. about 80 to 500 mrad upon irradiation with electron beam 22. A specimen image is displayed by brightness modulation of the scanning image display section 17 in synchronizing the signals from the detectors 6, 7, 8 with the scanning signals, whereby observation of the figure or crystalline structure of the specimen 15. The dark-field STEM image has a contrast reflecting the means atomic number of the specimen 15.

A TV camera for observing an electron beam diffraction image 10 is disposed below the detector 7 for observing the dark-field STEM image. The TV camera 10 for observing electron beam diffraction image is connected to a monitor 11 for electron beam diffraction image display by mans of the electron beam image analysis section 3. The EDX detector 9 for detecting characterization X-ray emitted from the irradiated specimen is disposed above the objective lens 14. The EDX detector 9 is connected to the EDX analysis section 2. The electron beam device control section 19, the EDX analysis section 2 and the electron beam diffraction image analysis section 3 are so connected as to cable of communicating with the material characterization section 4 by means of off-line and on-line data communication.

Figure 2:
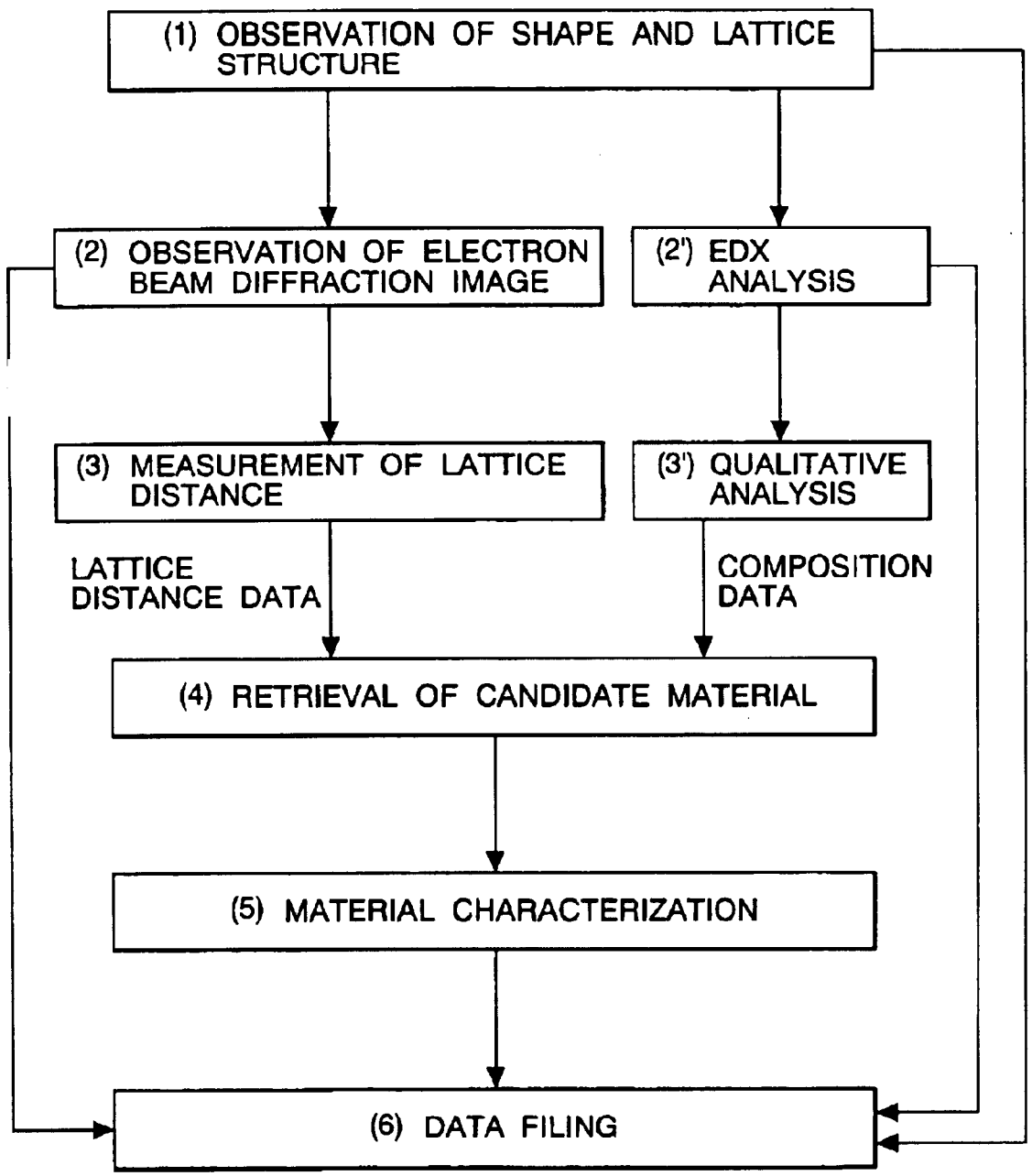
FIG. 2 is an explanation drawing showing the main processing procedure for the material characterization system shown in FIG. 1.

FIG. 2 is an explanation of processing for the material characterization system shown in FIG. 1.

(1) Electron beam is scanned on the specimen by scanning; then, observation of secondary electron, bright-field scanning transmission image, and dark-field scanning transmission image of the specimen thereby to observe the shape and crystal structure of the specimen. The observation results are stored in the electron beam control section 19. At the same time, the name of the file or image data are input in the material characterization section 4.

(2) The electron microscope is stopped at a position that is an object of observation. The electron beam diffraction image formed at this stage is taken into by the TV camera 10 for observation of the electron beam diffraction image. The displayed secondary electron image, bright-field scanning transmission image, and dark-field scanning transmission image are corrected so as to coincide with the direction of the images with that of the diffraction image. The corrected images are displayed on the monitor 11 for displaying electron beam diffraction images. Concurrently with the storing, the image file name or image data is input in the material characterization section 4.

(3) Selection of a method of measuring the lattice distance of a crystal (any one of the methods disclosed in FIGS. 6, 8, 12, 14) in accordance with the kinds of electron beam images displayed on the electron beam diffraction image monitor 11.

A measurement value R is determined by the selected measuring method. The lattice distance d is given $d=L\lambda/R$, where L is a camera length, $\lambda$ is a wave length of electron beam, and $L\lambda$ is a constant. Therefore, the lattice distance d can be acquired from the measured value R if $L\lambda$ is obtained using d, $\lambda$ of a known material in advance. The calculated lattice distance of the crystal is stored in the electron beam diffraction image analysis section 3, the date of which is input into the material characterization section 4.

(2') The EDX analysis starts concurrently with the step (2) above. The EDX spectrum obtained is stored in the EDX analysis section 2. Concurrently with the storage, the file name or EDX spectrum data is input into the material characterization section 4.

(3') A qualitative analysis of the material of the irradiated specimen with the electron beam is conducted from the EDX spectrum.

The acquired composition data is memorized in the EDX analysis section 2 and, at the same time, is input into the material characterization section 4.

(4) At the material characterization section 4, the data obtained at the above mentioned (3) and the composition data obtained at the above-mentioned (3') are verified; then substances corresponding to the data are retrieved.

(5) Characterization of the material is conducted at the material characterization section 4 to display the result.

(6) At the material characterization 4, the characterization result and a series of data (1) through (4) are stored with the same label.

Figure 3:
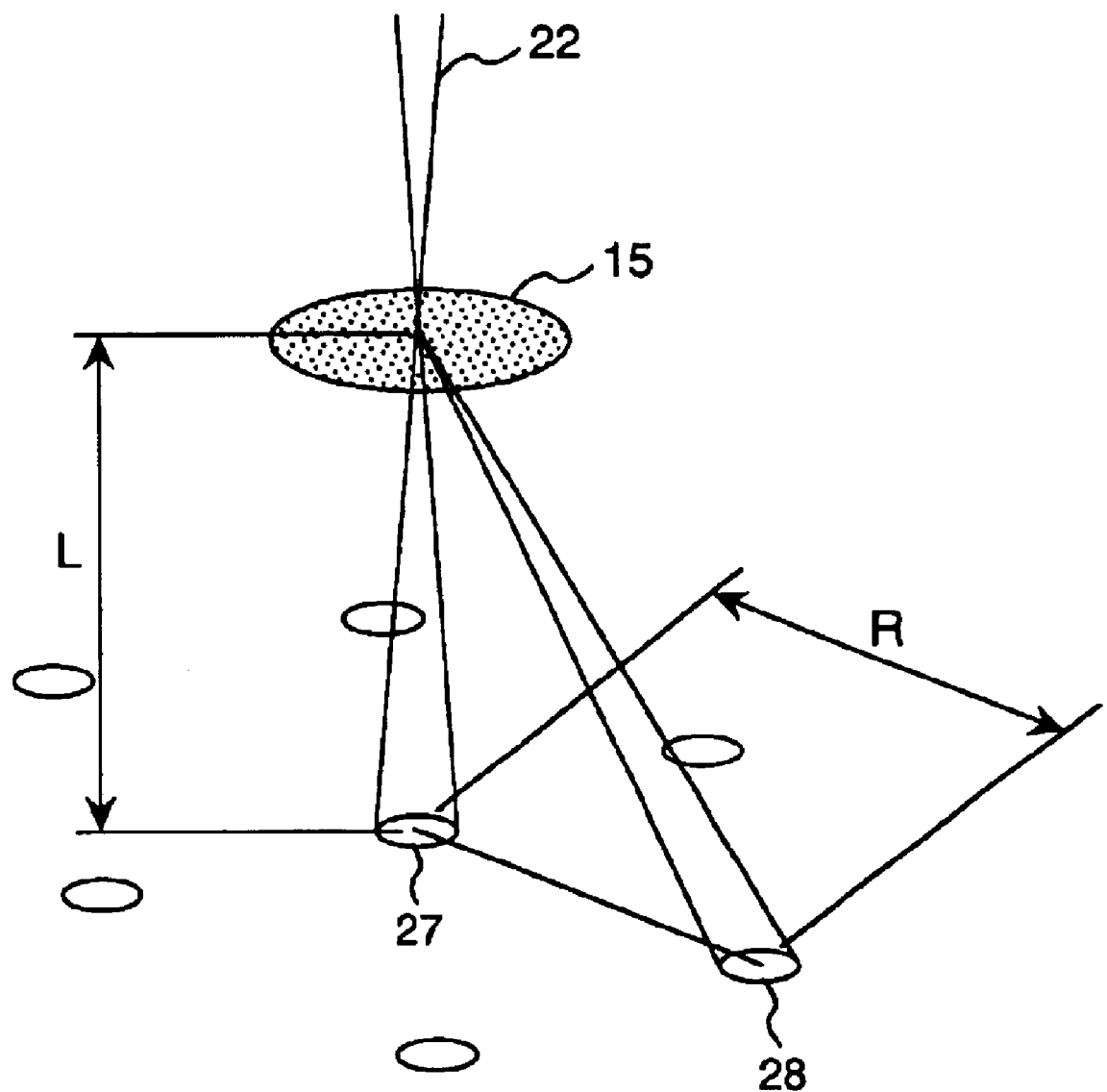
FIG. 3 is an explanation drawing of a nano-probe.

FIG. 3 is an explanation drawing of a nano-probe diffraction image generated at the time of irradiating a minute region of the specimen with a focused electron beam. The electron beam 22 emitted from the electron beam gun 12 is focused by the condenser lens 13 and the objective lens 14 and irradiated on the specimen 15. When the electron beam 22 is stopped at the region to be measured on the specimen 15, the electron beam 22 that has passed through the specimen 15 is subjected to diffraction by the specimen 15, thereby to form an electron beam diffraction image in the post-focus surface of the objective lens 14.

The electron beam diffraction image if then enlarged by the projection lens 24, and the photographed diffraction image is projected on a TV camera for observing the electron beam diffraction image. The photographed diffraction image is displayed on the monitor 11. The distance between the main spot 27 of the electron beam diffraction image and the diffraction spot 28 corresponds to the lattice distance of the specimen. The magnitude of the electron beam diffraction image can be altered by changing current value to the project lens 24.

If there is not the project lens, the distance between the specimen and the enlarged electron beam diffraction image is expressed as the camera length L, which is necessary for acquiring the same electron beam diffraction image as the electron beam diffraction image enlarged by the project lens. When the current value of the project lens 24 is altered, the direction of the electron beam diffraction changes. In this case, since the direction of the electron beam diffraction image does not coincide with the direction of observation angle, there is a problem when the orientation of the crystal is investigated. In the present invention, there is means for arranging the direction of the electron beam diffraction image and the direction observation view.

A method for arranging the direction of scanning the specimen and the direction of the electron beam diffraction image is explained by reference to FIGS. 4a to 4d. The position of the TV camera for observation of the electron beam diffraction image is mechanically adjusted so as to make the direction of the electron beam diffraction image of FIG. 4a coincide with the direction of the specimen scanning at a current value of the project lens 24, in advance. When enlarging the electron beam diffraction image, the electron beam diffraction image rotates concurrently with enlargement as shown by FIG. 4c.

Figure 4A:
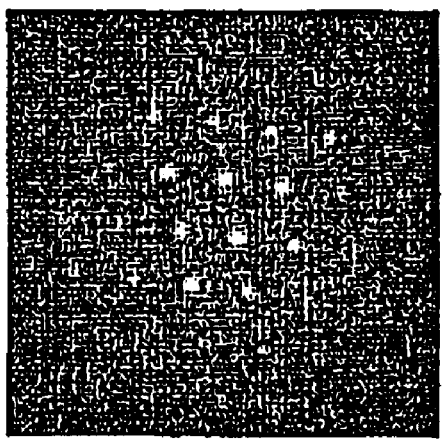
FIGS. 4a to 4d are photographic drawings for explanation of a method of coinciding with the electron beam diffraction image and the scanning direction of the specimen.
Figure 4B:
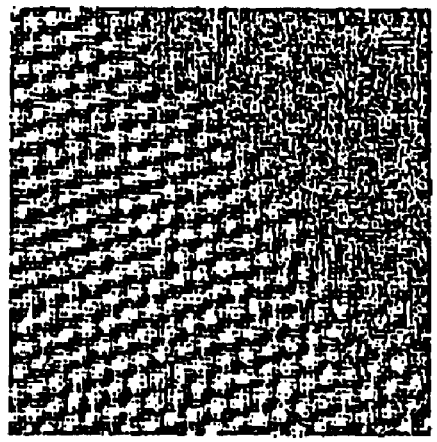

Generally, the relationship between a lens current value I of the project lens 24 and a rotation angle f of the image is expressed as $f=0.18NI/\sqrt{F0}$. In the equation, F0 is an acceleration voltage, N the number of winding, I a lens current. Accordingly, since the rotation angle f (Since the rotation direction is anticlockwise in FIG. 4c, the angle is shown as "-f".) of the electron beam diffraction image is seen from the current value of the project lens 24, alteration of the scanning direction of the electron beam 22 is given the scanning power source 18 from the control section for the electron beam device so as to rotate the specimen scanning image by the same angle as the rotation angle, i.e., the angle f. As a result, the specimen scanning image of FIG. 4d that has been rotated by the angle f from the specimen image of FIG. 4b is displayed on the scanning image display section 17.

Figure 4C:
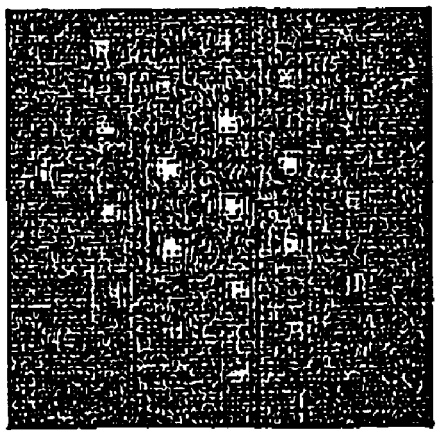
Figure 4C:
Figure 4D:
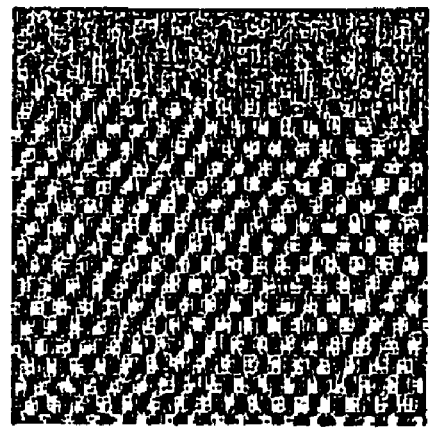
Figure 4D:

The direction of the thus displayed electron beam diffraction image of FIG. 4c coincides with the direction of the specimen scanning image of FIG. 4d.

FIGS. 5a to 5d explain another method of making the direction of the electron beam diffraction image coincide with the direction of the specimen scanning image. When the direction in FIG. 5a of the electron beam diffraction image and the direction in FIG. 5b of the specimen scanning image are in the same direction, the enlarged electron beam diffraction image in FIG. 5c rotates by the angle f (Since the rotation direction is clockwise, the angle is shown as "-f" in FIG. 5c.) with respect to the electron beam diffraction image of FIG. 5a. In this method, the electron beam diffraction image is returned to the former direction by rotating it on the monitor 11 for displaying the electron beam diffraction image backward by the angle f (Since the image that has rotated by -f is rotated backward, the angle is +f.).

Figure 5A:
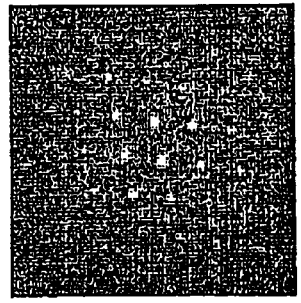
FIGS. 5a to 5d are photographic drawings for explanation of another method of coinciding with the directions of the electron beam diffraction image and the direction of the scanning image of the specimen.
Figure 5B:
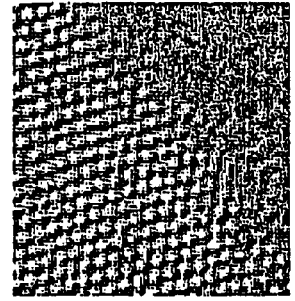
Figure 5C:
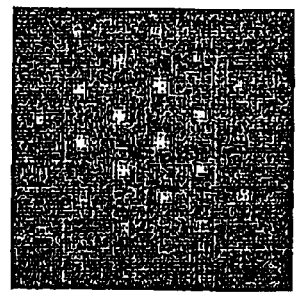
Figure 5C:
Figure 5D:
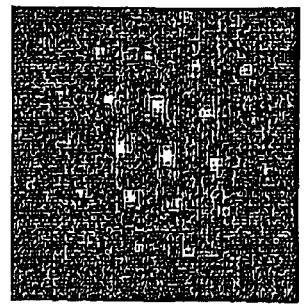
Figure 5D:

Concretely, an instruction for rotating the electron beam diffraction image of FIG. 5c is given the diffraction image analysis section 3 from the control section for the electron beam device so as to rotate the image having rotated by angle f (−f)by the angle −f (+f). In the diffraction image analysis section 3, the diffraction image of FIG. 5d that has been rotated by the angle −f (+f) is displayed on the monitor for the electron beam diffraction display 11. Like this, the specimen scanning image of FIG. 5b and the electron beam diffraction image of FIG. 5d, the directions being agreed, are acquired.

Then, a method of acquiring the lattice distance of a material from the electron beam diffraction image will be explained. The electron beam diffraction image exhibits different figures such as spot like or ring like forms according to the size of the crystal.

Figure 6A:
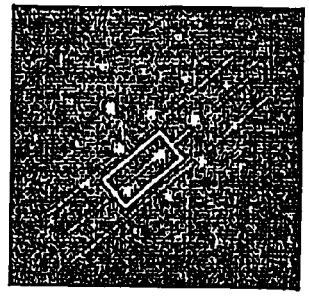
FIGS. 6a to 6e are drawings for explanation of an example for acquiring the lattice distance of the material.
Figure 6C:
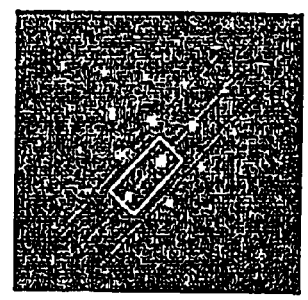
Figure 6B:
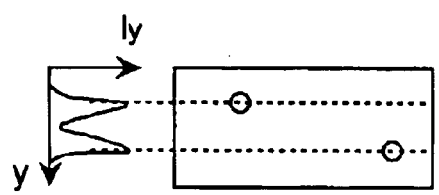
Figure 6D:
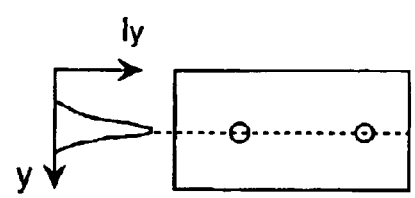
Figure 6E:
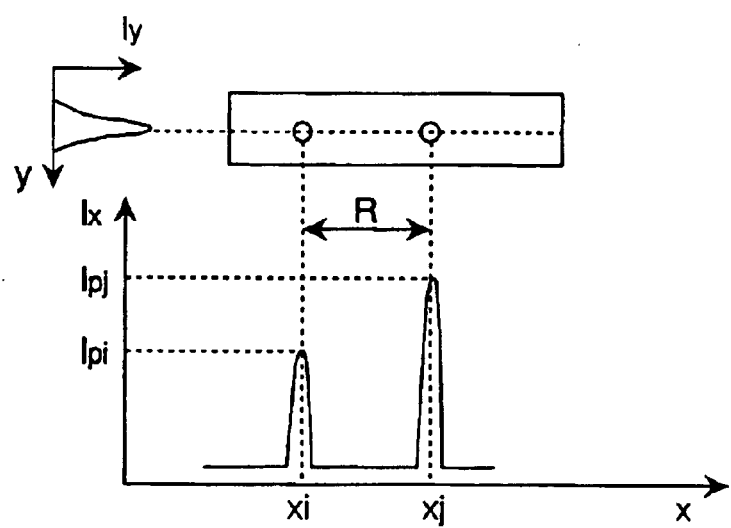
Figure 7:
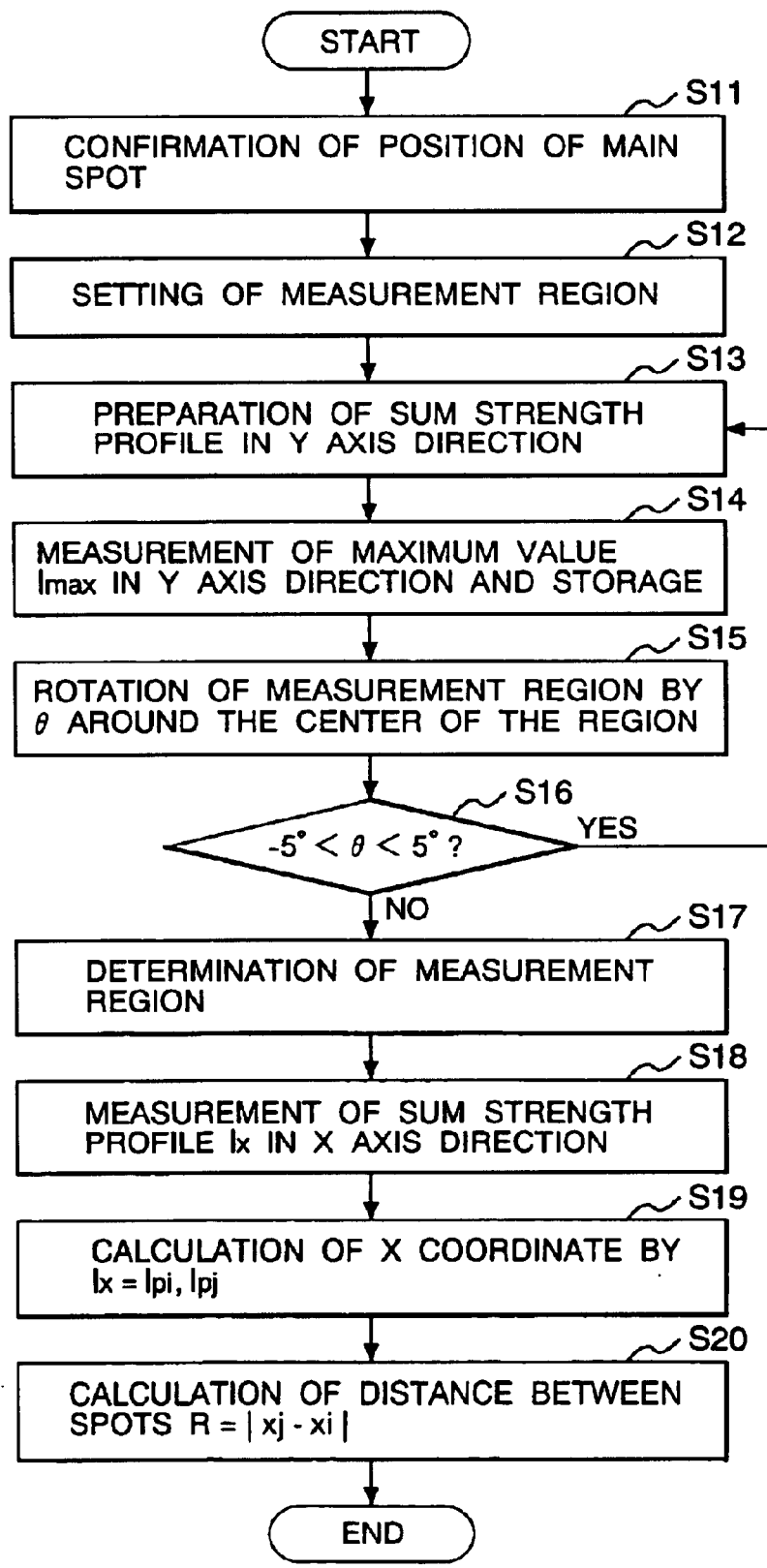
FIG. 7 is a drawing for explanation of the procedure for acquiring the lattice distance of the material.

FIGS. 6a to 6e explain an example of the method of acquiring the lattice distance from the distance between diffraction spots of the electron beam diffraction image. FIG. 7 is a flow-chart explaining the procedure of the method. At first, the position of the main spot in the electron beam diffraction image displayed on the monitor for displaying the electron beam diffraction image 11 is confirmed (S11 in FIG. 7). In order to do this, the fine specimen adjusting device 26 is operated. When the specimen 15 moves and if a spot remains, the spot is the main spot. Thus, its position is confirmed and the sight is returned.

Then, a measurement region that covers the main spot and one spot adjoining to the main spot is determined (S12 in FIG. 7). This is done by encircling the region in which the pair of the diffraction spots on the display with a square frame as shown in FIG. 6a.

In order to accurately measure the distance between the spots, it is necessary to measure the distance on the straight lines in parallel with the arrangement of the spots. So, a square that embraces the two diffraction spots is rotated within a certain angle θ (for example, ±5°), and the diffraction spots are arranged in the direction of the lengthwise axis of the square, as shown in FIG. 6c. Therefore, as shown in FIG. 6b, the sum of the pixel strength in the lengthwise direction at each of the short length sides (Y axis) of the square is calculated to obtain summed strength profile in the direction of Y axis (S13 in FIG. 7), thereby to acquire the peak value of the sum strength.

The measurement region designated by the square is rotated by 0.1°, for example, around the center of the measurement region, thereby to acquire the sum strength in the Y axis direction. The process of the peak value acquisition is repeated within the range of ±5° (S16 in FIG. 7). If the two diffraction spots are aligned in the lengthwise direction of the measurement region, the summed strength profile of the pixel in the Y axis direction exhibits one peak, which is the maximum as shown in FIG. 6d. Therefore, the measurement region in the angle exhibiting the maximum of the peak of the summed strength profile in the Y axis direction, which is measured by rotating the measurement region is determined (S17 in FIG. 7) as the measurement region for measuring the distance between the diffraction spots.

In the determined measurement region, the summed pixel strength in the short axis (Y axis) at each of the lengthwise axis (X axis) of the square is calculated to measure the summed strength profile in the X axis (S18 in FIG. 7). Then, as shown in FIG. 6 (e), the X coordinate $x_i$, $x_j$ of two peaks appearing in the measured sum strength profile is calculated (S19 in FIG. 7) to calculate the distance R (=$|X_j-x_i|$ between the spots (S20 in FIG. 7).

The lattice distance d is given d=Lλ/R. L is a camera length, λ a wave length of the electron beam; since Lλ is a constant, the lattice distance d can be acquired from the measured value R if the Lλ is acquired using a known material in advance. These processing is done by the electron beam diffraction analysis section 3; the obtained value is transferred to the material characterization section 4.

When spots are distributed homogeneously in the electron beam diffraction image, the measurement of the spot distance is done only once. However, if there is a pair of spots which have spots adjoining thereto, a new region where new different spots may appear is set, and then step 12 through step 20 are repeated to measure the lattice distance from the diffraction spots.

There is a case where only one measured value of the lattice distance is obtained or plural measured values are obtained. This is common to the following case where the lattice distance is measured by another method, which will be explained hereinafter.

Figure 8A:
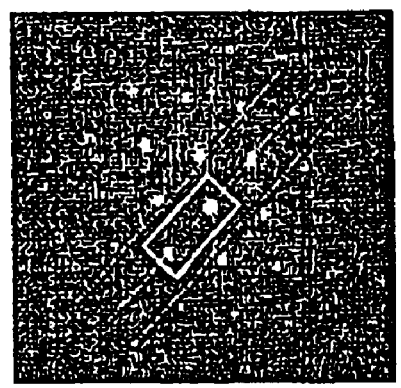
FIGS. 8a and 8b are drawings of another example of a method of acquiring the lattice distance of the material.
Figure 8B:
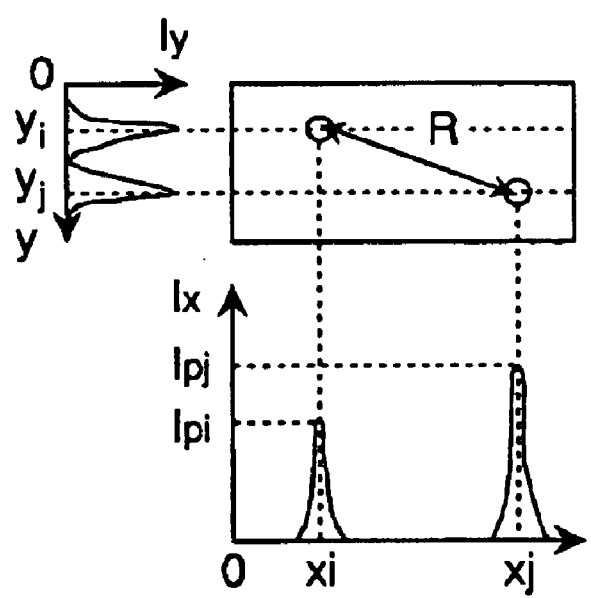
Figure 9:
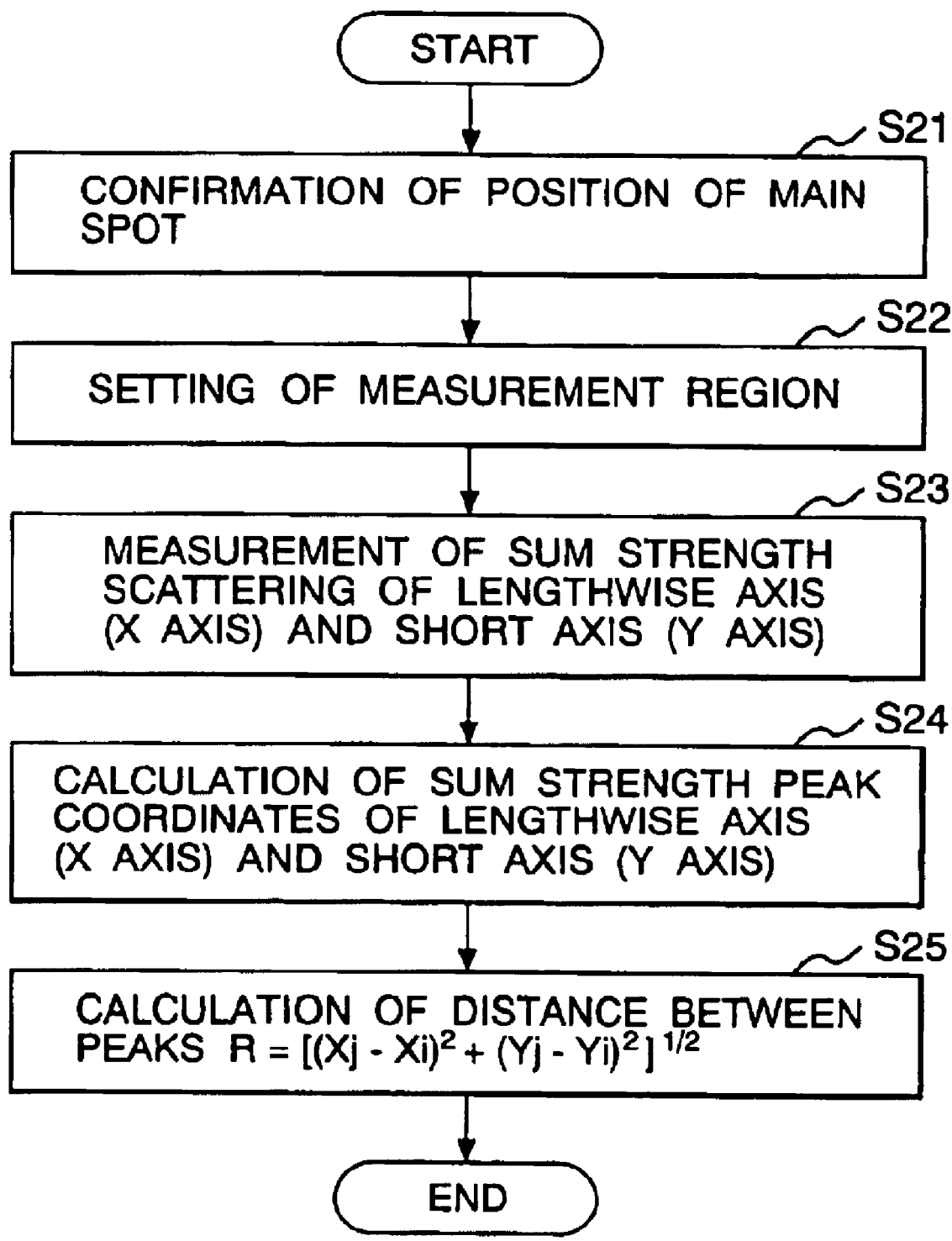
FIG. 9 is a drawing for explanation of the procedure for acquiring the lattice distance of the material.

FIGS. 8a and 8b explain a method of acquiring the lattice distance of a material from the distance between the diffraction spots of the electron beam diffraction image. FIG. 9 is a flowchart for explaining the procedure. At first, the position of the main spot is confirmed (S21 in FIG. 9). Then, as shown in FIG. 8a, the measuring region embracing the main spot and spot adjoining the main spot is set (S22 in FIG. 9). The step 21 and step 22 are the same as the procedure explained as the step 11 and step 12 in FIG. 7.

Next, as shown in FIG. 8b, the pixel strength in the direction of X axis is calculated as the X axis being long axis of the square measurement region and the short axis being Y axis. Similarly, the sum of the pixel strength in the Y axis is calculated to acquire the sum strength profile in the Y axis (S23 in FIG. 9). Then, the distance R=$[(x_i-x_j)^2+(y_1-y_2)^2]^{1/2}$ between the peaks is calculated (S25), based on two peak coordinates ($x_i$, $y_i$), ($x_j$, $y_j$), which correspond to the two diffraction spots. In the step 25, the equation represents relationship between the peak distance R and coordinates ($x_i$,$y_i$), ($x_j$, $y_j$). The R is calculated by the equation $\{(x_j-x_i)^2-(y_j-y_i)^2\}^{1/2}$. The equation in FIG. 13 at step 48 has the same meaning mentioned above.

Figure 10A:
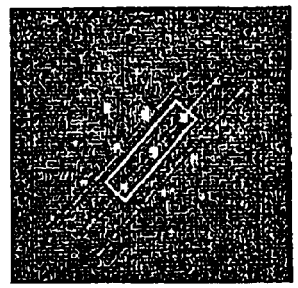
FIGS. 10a to 10d are drawings of a diagrammatic explanation of a method for acquiring the lattice distance of the material from the symmetric spots with respect to the main spot.
Figure 10B:
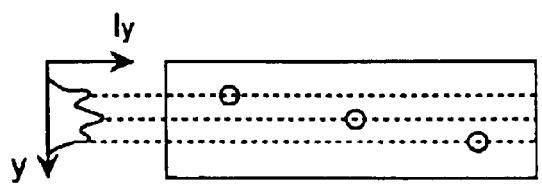

If the peak distance R is determined, the lattice distance d is calculated using the relationship d=Lλ/R. Then, a method of the lattice of a material in case where a spot symmetric to the main spot is explained, using the flow chart of FIG. 11 and the diagrammatic explanation shown in FIGS. 10a to 10d. In this example, as shown in FIGS. 10a, a square in which the main spot between spots are embraced is set to the electron beam diffraction image displayed on the monitor for the electron beam diffraction image, the spots being located at symmetrical position with respect to the main spot.

The position of the main spot can be confirmed by the manner as having been explained for the steps in FIG. 7. Then, as is diagrammatically shown in FIGS. 10a to 10d, the sum of the pixel strength in the direction the lengthwise axis (X axis) at each of points on the short axis (Y axis) of the square is calculated to acquire the sum strength profile in the direction of the Y axis.

Figure 10C:
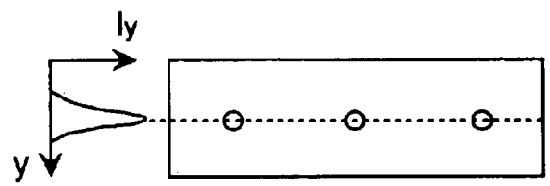
Figure 10D:
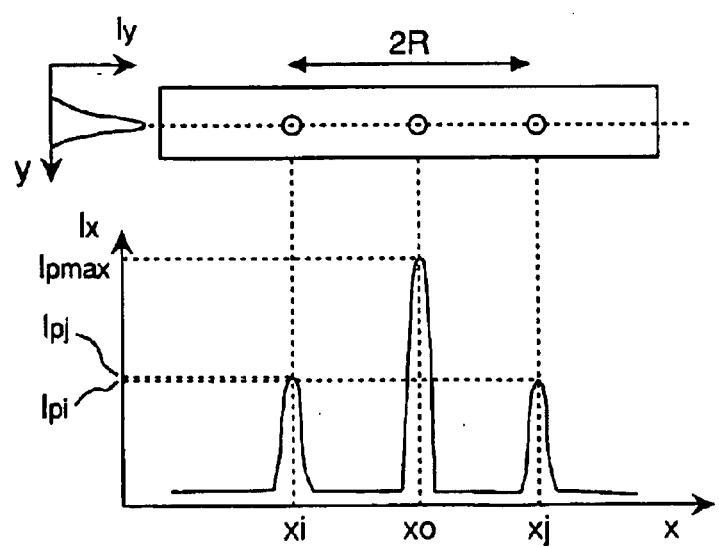
Figure 11:
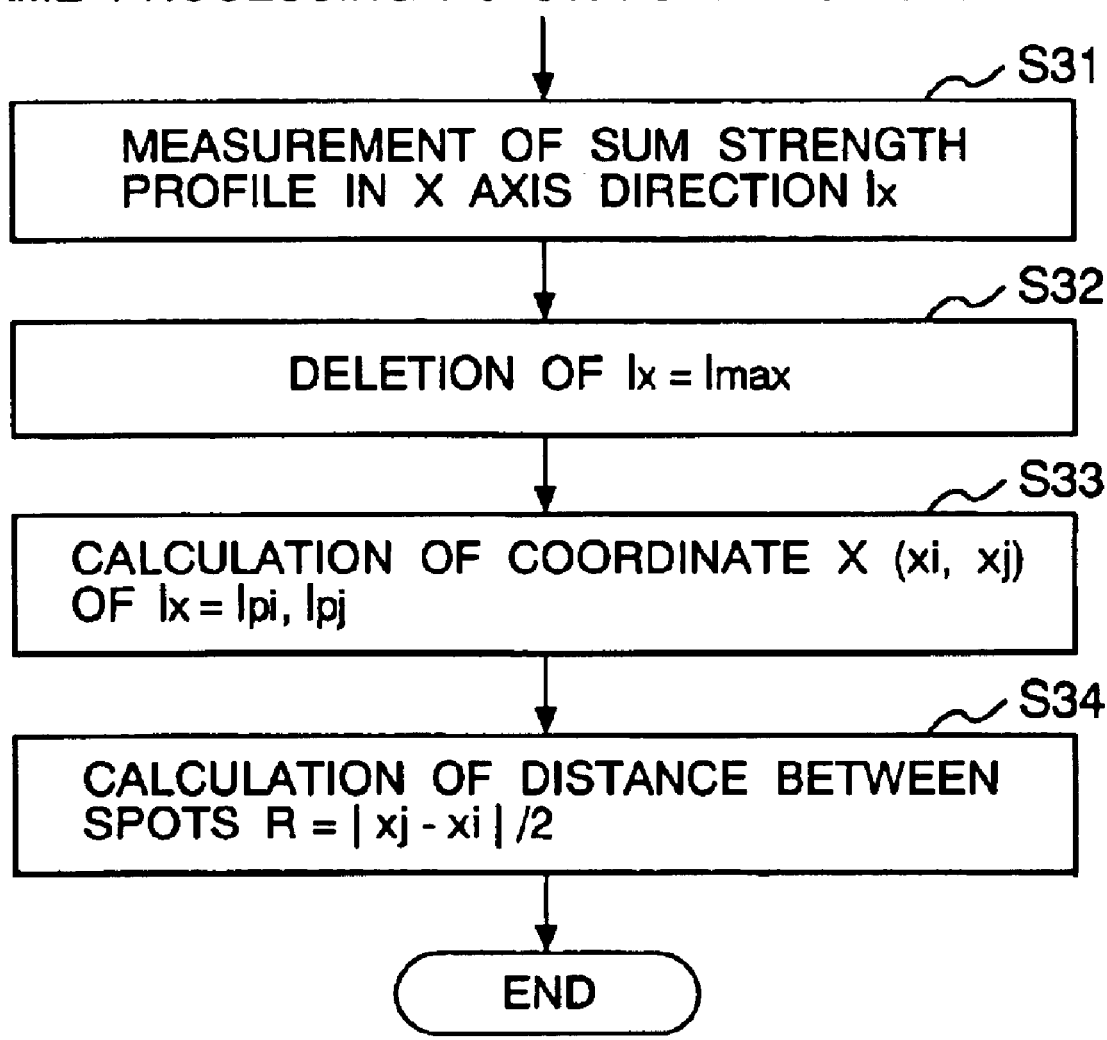
FIG. 11 is a flow chart of a method for acquiring the lattice distance of the material from the symmetric spots with respect to the main spot.

In order to measure the distance between the spots, it is necessary to measure the distance on the straight lines in parallel with the arrangement of the spots. Thus, the square region that embracing the three diffraction spots including the main spots is turned by a certain range of angle, so that the peak appearing in the profile of the sum value of the pixel strength in the Y axis becomes one as shown in FIG. 10c. The position which exhibits the maximum strength is set as the measuring region. The procedure having been described is almost the same as that comprising the step 11 to step 16 explained in FIG. 7.

Next, the profile of the sum value of pixel strength in the X axis direction (lengthwise axis) (S31 in FIG. 11) is acquired. Thereafter, in the profile of the sum value of the pixel strength in the direction of X-axis (lengthwise direction), the coordinate $x_0$ where the sum value of the pixel strength corresponding to the main spot becomes $I_x = I_{max}$ that is deleted (S33 in FIG. 11). Then, the $X_i$ and $x_j$ coordinates of the two peaks remained in the profile of the sum value of the pixel strength in the X-axis (lengthwise direction) are calculated. And, the distance between the spots $R=|x_j-x_i|/2$ is calculated using the acquired two coordinates $x_i$, $x_j$. The lattice distance is calculated by the equation $d=L\lambda/R$ as having explained.

Figure 12A:
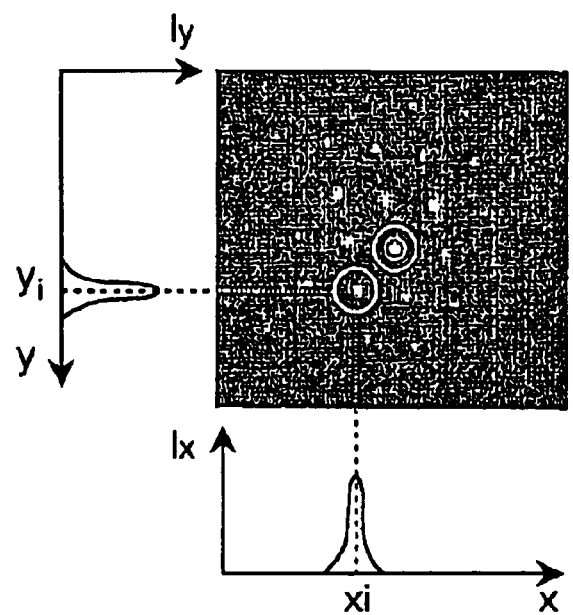
FIGS. 12a and 12b are drawings of explanation of another procedure for acquiring the lattice distance of the material.

Another method of acquiring the lattice distance regardless of whether the arrangement of the spots is symmetrical or asymmetrical will be explained, using the diagrammatic drawing of FIGS. 12a and 12b and the flow chart of FIG. 13. At first, the position of the main spot in the electron beam diffraction image displayed on the monitor for the electron beam diffraction image is confirmed (S41 in FIG. 13). This confirmation is done by the manner explained at the step 11 of FIG. 7. Then, as shown in FIG. 12a, the first measuring region with respect to the electron beam diffraction image is set to designate one of the pair of spots (S42 in FIG. 13).

This designation is done by selecting a desired spot with a circle embracing it, for example. Further, it is desirable to select the main spot or the spot adjoining to the main spot. When the spot is designated, the sum strength profiles in the X axis and Y axis directions are acquired (S43 in FIG. 13), and X coordinate xi where the sum strength profile in the X axis direction exhibits the maximum and Y coordinate yi where the sum strength profile in the Y axis direction exhibits the maximum are acquired (S44 in FIG. 13).

Figure 12B:
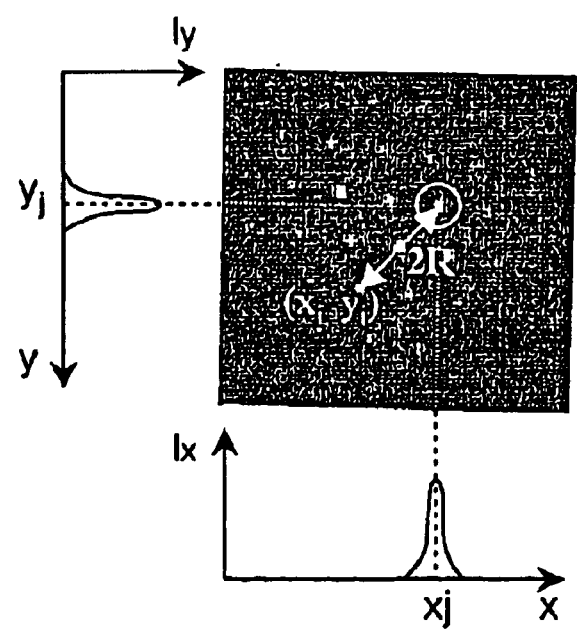
Figure 13:
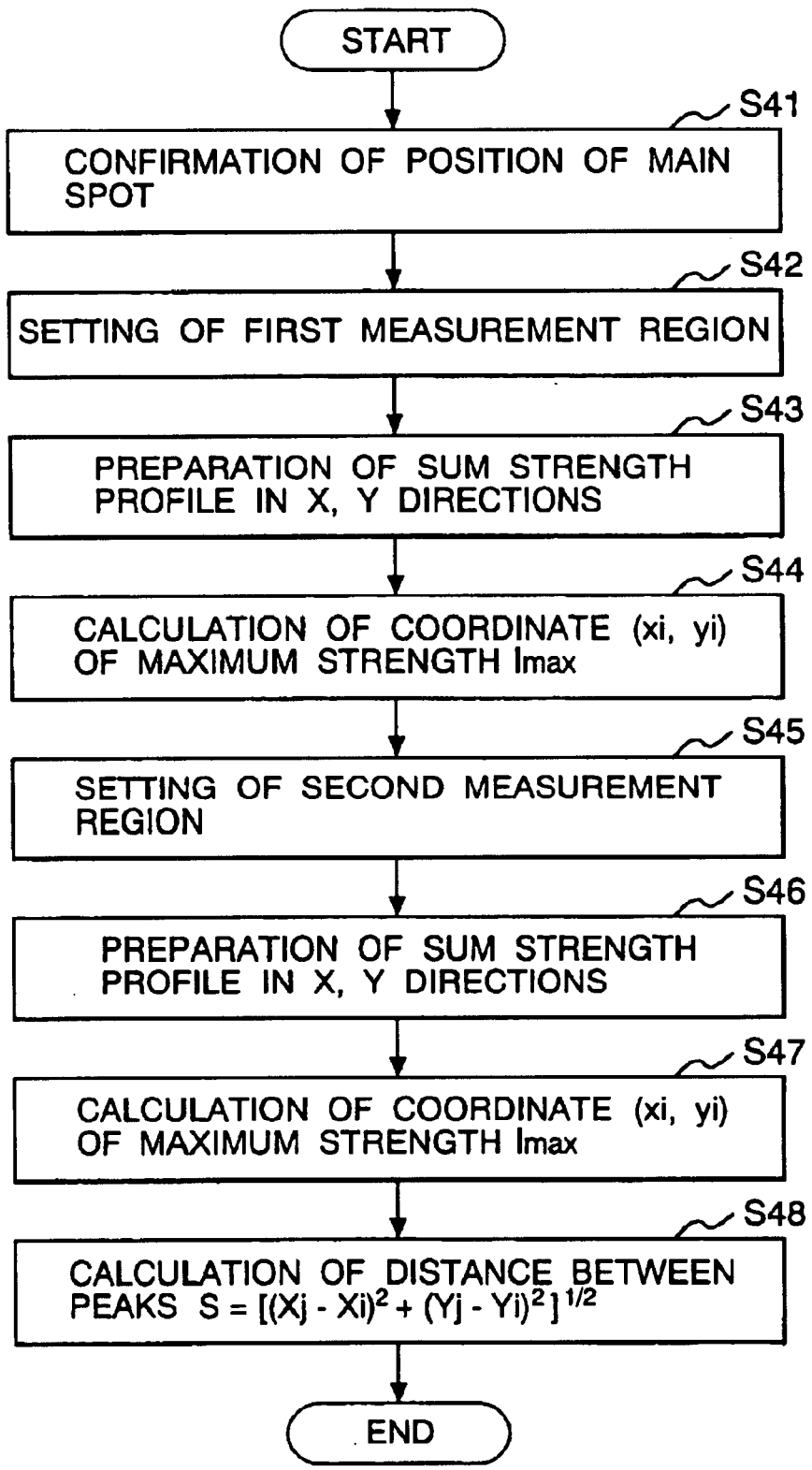
FIG. 13 is a flow chart of a procedure of a method for acquiring the lattice distance of the material.

Then as shown in FIG. 12b, the second measuring region with respect to the electron beam diffraction image is set to select the other spot for acquiring the distance between the spots (S45 in FIG. 13). The selection of the second spot is done by circling the desired spot with a circle. The spot selected as the second spot is the one adjoining to the main spot, when the spot previously selected is the main spot. When the spot previously selected is the one adjoining to the main spot, the spot selected here is preferably the spot at symmetrical position with respect to the main spot.

Then, as similar to the first spot, the sum strength profile in the X axis and Y axis directions in the second measuring region is acquired (S48 in FIG. 13), and then, X coordinate $x_j$ where the sum strength profile exhibits the maximum in the X axis direction and Y coordinate $y_j$ where the sum strength profile in the Y axis direction exhibits the maximum are acquired (S47 in FIG. 13).

If the measurement of the two spots is over, the distance $S=\{(x_j-x_i)^2+(y_j-y_i)_2\}^{1/2}$ is calculated (S48 in FIG. 13). Here, the value of R is acquired in accordance with R=S/2 or R=S under the condition of whether the selected pair of spots are the symmetrical spots (2R) sandwiching the main spot or the main spot is included (R). The lattice distance d is calculated by the equation $d=L\lambda/R$. In the case where measurement of another spots pair is conducted, the processing is repeated after returning to the step 42.

Figure 14A:
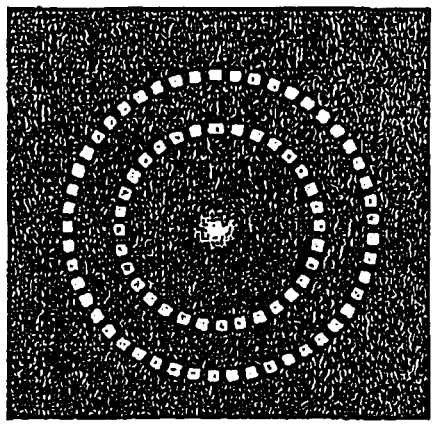
FIGS. 14a to 14b are diagrammatic drawings of a procedure for acquiring the lattice distance of the material from the electron beam diffraction image of a ring shape.
Figure 14B:
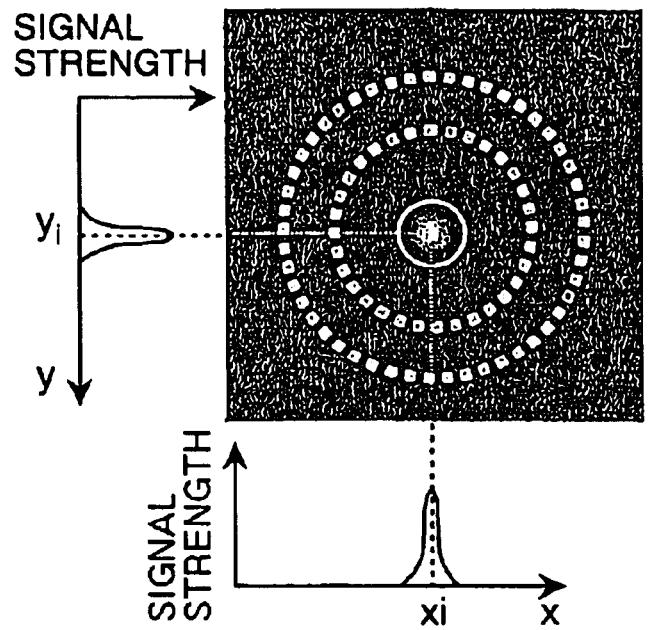
Figure 15:
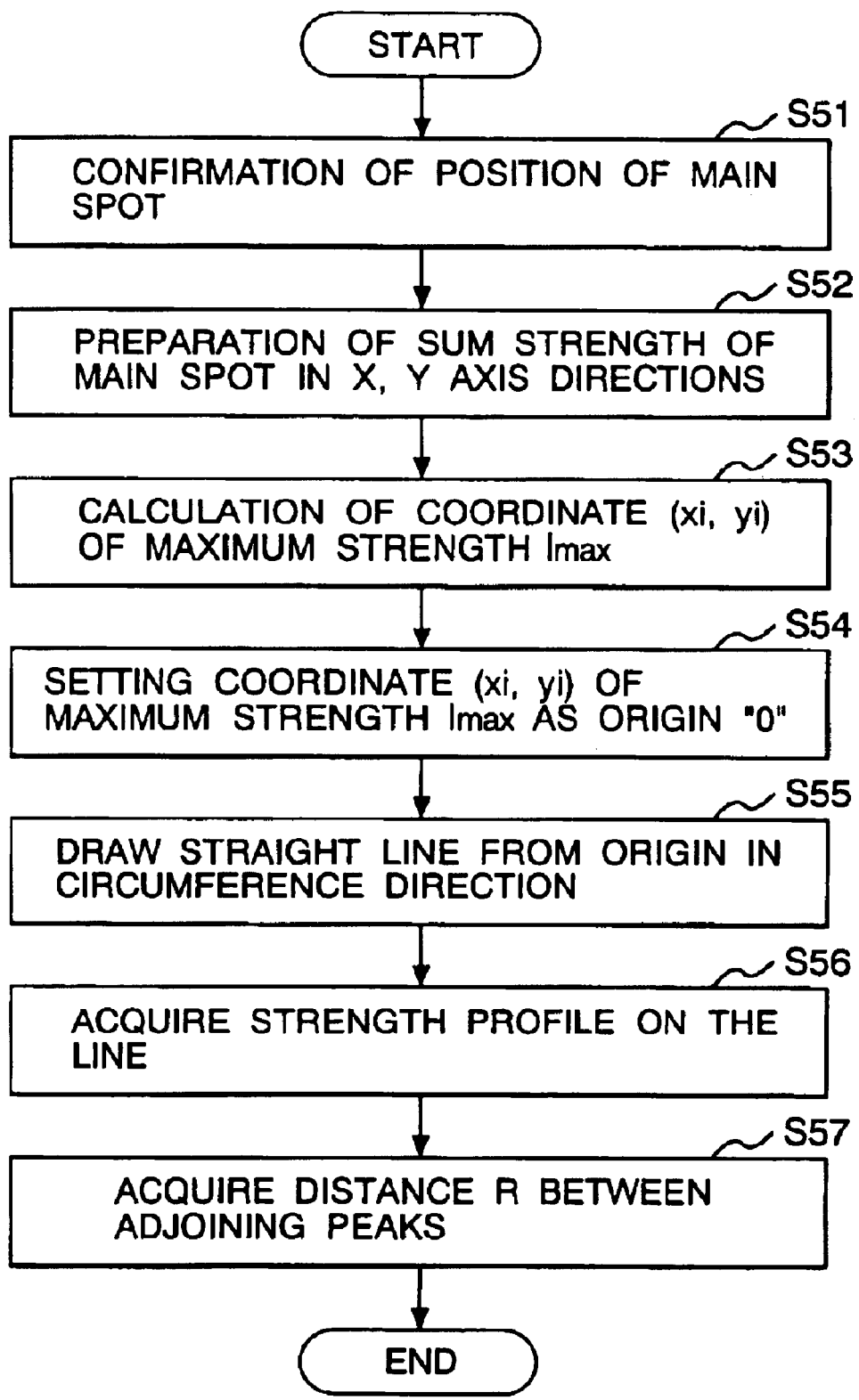
FIG. 15 is a flow chart of a procedure for acquiring the lattice distance from the electron beam diffraction image of a ring form.

Then, a method of measuring the distance is explained in the case where the electron beam diffraction image is a ring shape by way of the diagrammatic view of FIGS. 14a to 14b and the flow chart of FIG. 15.

FIG. 14a is a diagrammatic view showing an electronic beam diffraction image of a ring shape. The spot located at the center is the main spot, and the electron beam diffracted by the specimen distributes around the main spot in the form of the ring.

At first, the position of the main spot is confirmed on the monitor 11 for observing the electron beam diffraction image (S51 in FIG. 15). Then, as shown in FIG. 14b, the main spot is encircled with a circle to designate a region to acquire the sum strength profiles in the directions of X axis and Y axis of the main spot in the region (S52 in FIG. 15). And, the coordinates (xi, yi) of the main spot are acquired from peaks of the sum strength profiles in each of the directions (S53 in FIG. 15). The processing until this step is carried out in the same manner as step 41 to step 44 explained in FIG. 13.

Figure 14C:
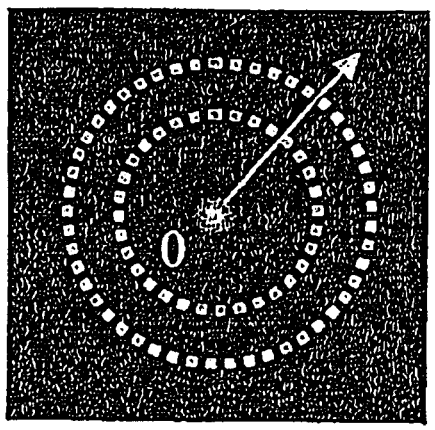
Figure 14D:
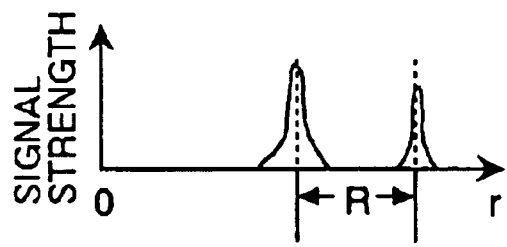

Then, a straight line is drawn from the origin so as to transverse the diffraction ring, as shown in FIG. 14c, where the coordinates of the main spot is the origin (S55 in FIG. 15). And, the strength profile is acquired on the straight line (S56 in FIG. 15). FIG. 14d is a diagrammatic view of the acquired strength profile.

Then, the distance R between the adjoining peaks of the strength profile (S57 in FIG. 15). The lattice distance d is calculated by the equation $d=L\lambda/R$ as described before. When the distance R between the adjoining peaks is different from the other distance based on the positions on the strength profiles, plural values are obtained as the lattice distance.

In any of the measurement methods having been described with reference to FIGS. 6a through 15, the positions of the strength profile are preferably acquired with high accuracy by fitting the strength profile to the parabola or Gauss' distribution, etc. wherein the optimum fitting positions are set as peak positions.

According to this method, the distance between the center spot of the electron beam diffraction and the diffraction spot, which was difficult to measure with high accuracy, can be measured with high accuracy, and to calculate the lattice distance with high accuracy.

Figure 16:
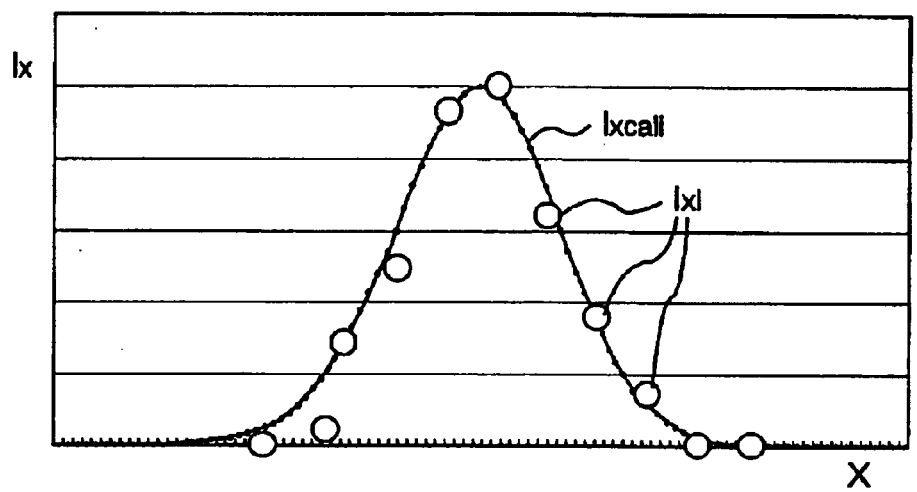
FIG. 16 is a drawing of explanation of a method for acquiring the peak position of the strength profile.

FIG. 16 explains a method of acquiring the peak position of the strength profile by fitting to the normal distribution, etc. For example, coordinate X is given each of the regions to be taken. When the X coordinate of i-th pixel is xi, and when the strength is Ix, the measured value is plotted as o. The parabola to be fitted is expressed as the equation (1).

(Equation 1)

$$I_{xcali}=-ax_i^2+bx_i+c \quad (1)$$

Coefficients a, b and c are acquired by the minimum power, method, for example, so as to be closest to each other. That is, the coefficients a, b and c are acquired by, for example, the least square method. Tat is, they are decided to be that the sum S of the squares of the error e is the minimum according to equations (2) and (3). Here, n is the number of pixels in the region to be taken into.

(Equation 2)

$$e_i=I_{xi}-I_{xcali} \quad (2)$$

$$S = \sum_{i=1}^{n} e_i^2 \quad (3)$$

In case of acquiring the peak position by fitting to the normal (Gauss') distribution, the average value $\mu$, distribution s and standardization constant a are decided by using the following equation (1') instead of equation (1). In acquiring these parameters $\mu$, s and a, the equations (2) and (3) are used, as mentioned before.

(Equation 3)

$$I_{xcali} = a \exp\left\{-\frac{(x_i - \mu)^2}{2\sigma^2}\right\} \quad (1')$$

Next, an analysis of composition according to EDX analysis will be explained. In carrying out the analysis of composition by EDX analysis, the electron beam 22 is stopped at the measurement object region 15. Then, characterization X-ray having energy corresponding to the composition is emitted from the region. The characterization X-ray is detected by the EDX detector 9, and at the EDX analysis section of the EDX detector, processing of the electric pulse wave height corresponding to the energy of the detected X-ray is conducted.

The processing result is displayed on the display section 23 of the EDX analysis section 2 as spectrum arranged in the order of energy. Further, at the EDX analysis section 2, signal processing of quantitative calculation using the spectrum is carried out. The result of processing is transferred to the material characterization section 4.

In determining elements contained based on the result of the EDX analysis, it is necessary to take into consideration whether the characterization X-ray detected by the EDX detector is emitted from the specimen 15 or system X-ray emitted from the neighborhood of the irradiation lens system of the electron beam device 1 or stray light X-ray emitted from the region other than irradiated region with electron beam, X-ray emitted from the region other than the analytical region must be deleted from the analytical object.

Figure 17A:
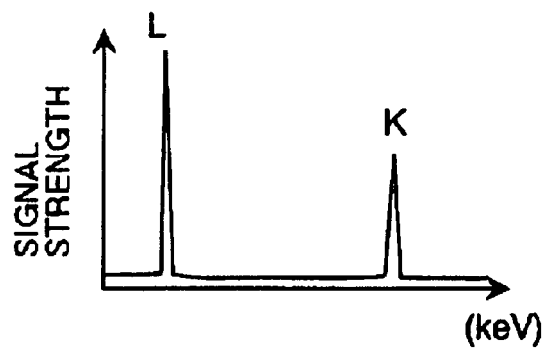
FIGS. 17a and 17b are spectroscopic diagrams of a detected spectrum of the characterization X-ray.
Figure 17B:
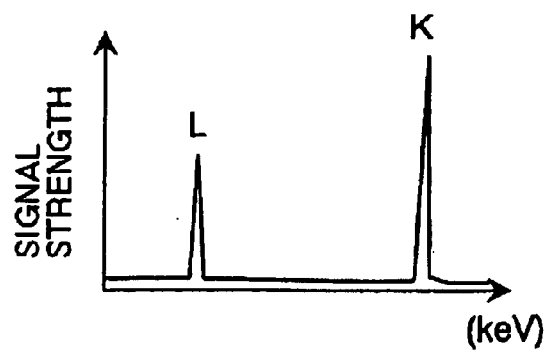
Figure 18:
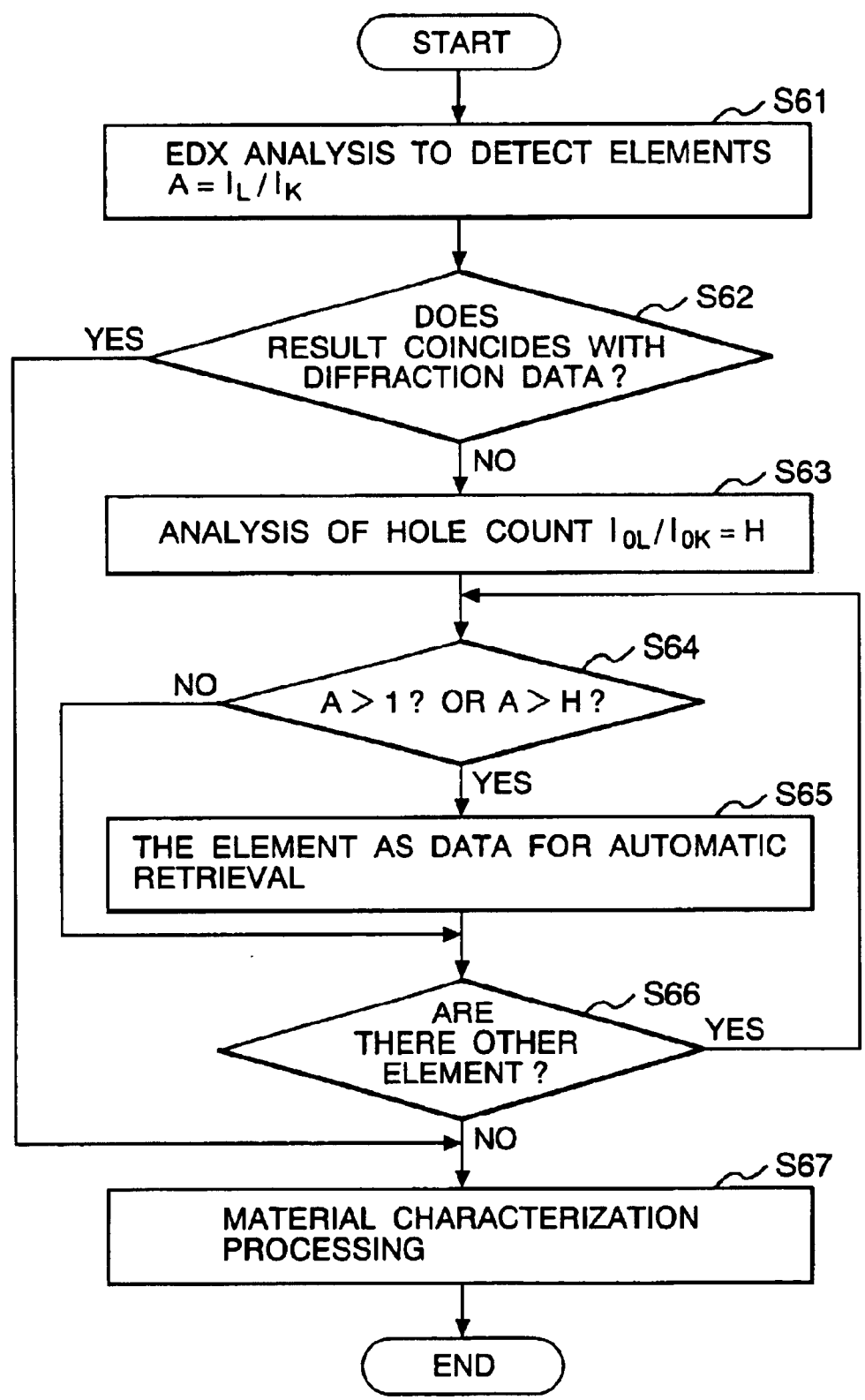
FIG. 18 is a drawing of explanation of a method for carrying out the EDX analysis by automatic elimination of the X-ray emitted from the region other than the analysis object.

The present invention provides a system for carrying out the EDX analysis wherein the X-ray emitted from the region other than the analytical region is automatically deleted. The system is explained with reference to FIGS. 17a, 17b and 18. FIGS. 17a and 17b show an example of detected characterization X-ray spectrum, and FIG. 18 is a flow chart showing a procedure for acquiring elements in the analytical region.

The analytical result of EDX is displayed on the display section 23 as spectra shown in FIGS. 17a and 17b. The horizontal axis is energy of X-ray, and the vertical axis is signal strength. The characterization X-ray, which is emitted when electrons of L kernel transit to the vacancy formed by shooting electrons out with irradiation electron beam from the K nucleus is called Ka ray, while characterization X-ray emitted when electrons transit from M nucleus to L nucleus is called La ray.

Supposing that when X-ray is detected without absorption in the specimen, which X-ray is emitted from the specimen 15 by irradiation with the electron beam, a spectrum of La ray having higher strength as shown in FIG. 17a than Ka is detected.

When characterization X-ray of structure members is emitted by irradiation of the focus of the irradiation system for trimming the spread of electron beam, not by irradiation with electron beam, or when electron beam scattered by the specimen excites the structure members, the strength of Ka is higher than La, as shown in FIG. 17b.

When plural elements are concurrently excited by the electron beam irradiation, plural Ka rays and plural La rays are emitted. Since the energy values of Ka ray and La ray of the respective elements are known, it is easy to find pairs of Ka ray and La ray.

In the present invention, the composition in the analytical region by the procedure shown in FIG. 18 is acquired in light of the above-mentioned phenomenon.

At first, the EDX analysis of the objective region is carried out. Elements that are never contained are removed at this step. At the EDX analysis section 2, a strength ratio $A=I_L/I_K$ of Ka ray and La ray is calculated with respect to Ka ray and La ray that are detected among the detected elements (S61 in FIG. 18).

Information of the detected remaining elements is input from the EDX analysis section 2 into the material characterization section 4. In the material characterization section 4, data inputted from the EDX analysis section 2, data inputted from the electron beam diffraction image analysis section 3 are compared with automatic retrieval data (S62 in FIG. 18). When the both data are in coincidence, the material characterization processing is carried out using the data (S67 in FIG. 18).

When the combination does not coincide with judgment at the step 62, or when the number of elements detected by the EDX is too large, analysis at a position near the edge of the specimen 16 is carried out by the electron beam thereby calculate the strength ratio of La ray and Ka ray $H=I_{0L}/I_{0K}$ (S63 in FIG. 18) with respect to the detected elements, the position being in the neighborhood of the analytical region. The hole-count in the step 63 means the number of counts of characteristic X-ray detected when a focused electron beam is injected into a hole (i.e. there is no specimen). Although the X-ray due to the hole-count should not be detected, the excited X-ray may be detected when the insufficiently focused electron beam scatters to excite the electron microscope mirror tube. Thus, it is necessary to investigate the hole-count.

Then, the strength ratio of La ray and Ka ray H is compared with the strength ratio of La ray and Ka ray A (S64 in FIG. 18) as H/A. In case of $A \geq 1$, i.e. $I_L \geq I_K$, the detected X-ray can be regarded as the characterization X-ray emitted from the analytical region. Thus, the data can be used as the retrieval data for material characterization of the elements (S65 in FIG. 18). In case of A<1, comparison of A and H is done; if A>H, the X-ray can be regarded as the characterization X-ray emitted from the analytical region.

Thus, the result can be used as the automatic retrieval data for processing material characterization (S65). In case of A<1 and $A \leq H$, the characterization X-ray is regarded as one emitted from the region other than analytical region, and the data is deleted from the automatic retrieval data. This processing is carried out for respective elements detected by the EDX analysis (S66 in FIG. 18). Thereafter, the material characterization section carries out material characterization based on the remaining elements (S67 in FIG. 18).

According to this, the X-ray that may be emitted from the region other than the analytical region is removed from the analytical object, and hence the material characterization can be carried out with high accuracy.

FIG. 19 shows an example of data stored in the material characterization section 4. The material characterization section 4 stores data base 53 for retrieval of characterization processing. In addition to the data, the lattice distance data 51 transferred from the electron beam diffraction image section 3 and the composition (elements) data transferred from the EDX analysis section 2 is added thereto. The retrieval data base 53 stores manes of materials (or chemical formulas, chemical structures), their compositions (element composition) and the lattice distance are stored as a set.

In the material characterization section 4, possible compounds are picked up from the retrieval data base, based on the composition data 52 acquired by the analysis of the specimen. Then, the lattice distance of the picked up candidate compounds is compared with the measured lattice distance 51 to retrieve a compound having the same values as the data, and the compound is stored. In case of the example shown in the drawing, if the composition coincides with the composition data 52, the material 54 having the lattice distance that coincides with measured lattice distance 51 is retrieved to display on the display section and to sore it.

Figures 20, 21:
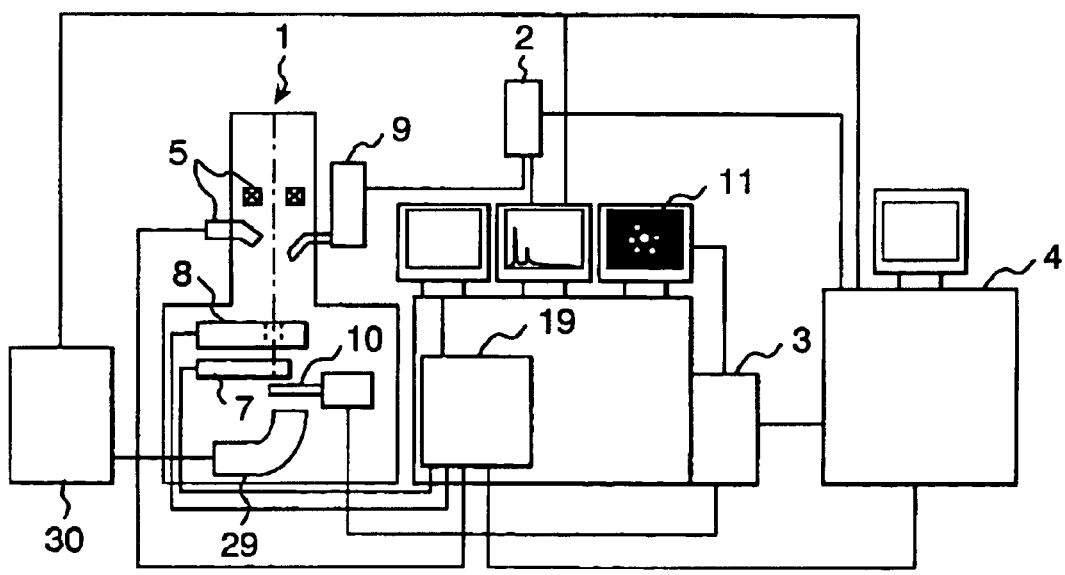
FIG. 20 is an example of a data storage format at the material characterization section.
FIG. 21 is another example of the material characterization section according to the present invention.

FIG. 20 shows an example of a data storage format in the material characterization section 4. As shown in this example, the data obtained from the one analytical view of the specimen is filed under one name in the following order.
(1) The file name of file recording the image data or images of secondary electron images or transmission electron images, etc.
(2) The file name of image data of the electron beam diffraction image or the file recording the images
(3) The file name of the EDX spectrum data or the file recording the images
(4) The lattice distance data
(5) Composition data
(6) Retrieval data According to the file storage format, the specimen image, electron beam diffraction image, EDX analytical result and material characterization result of one analytical region are stored as a set, and the retrieval of the data becomes easy.

FIG. 21 shows a diagrammatical view of an example of the material characterization system of the present invention. The material characterization system of this example is provided with an electron energy loss spectroscopy (EELS) 29 below the TV camera 10 for the electron beam diffraction image. EELS spectroscopy 29 is connected to the material characterization section 4 by way of EELS analysis section 30. EELS can be used in place of EDX or EDX and EELS are used together to conduct a qualitative analysis.

Figure 22:
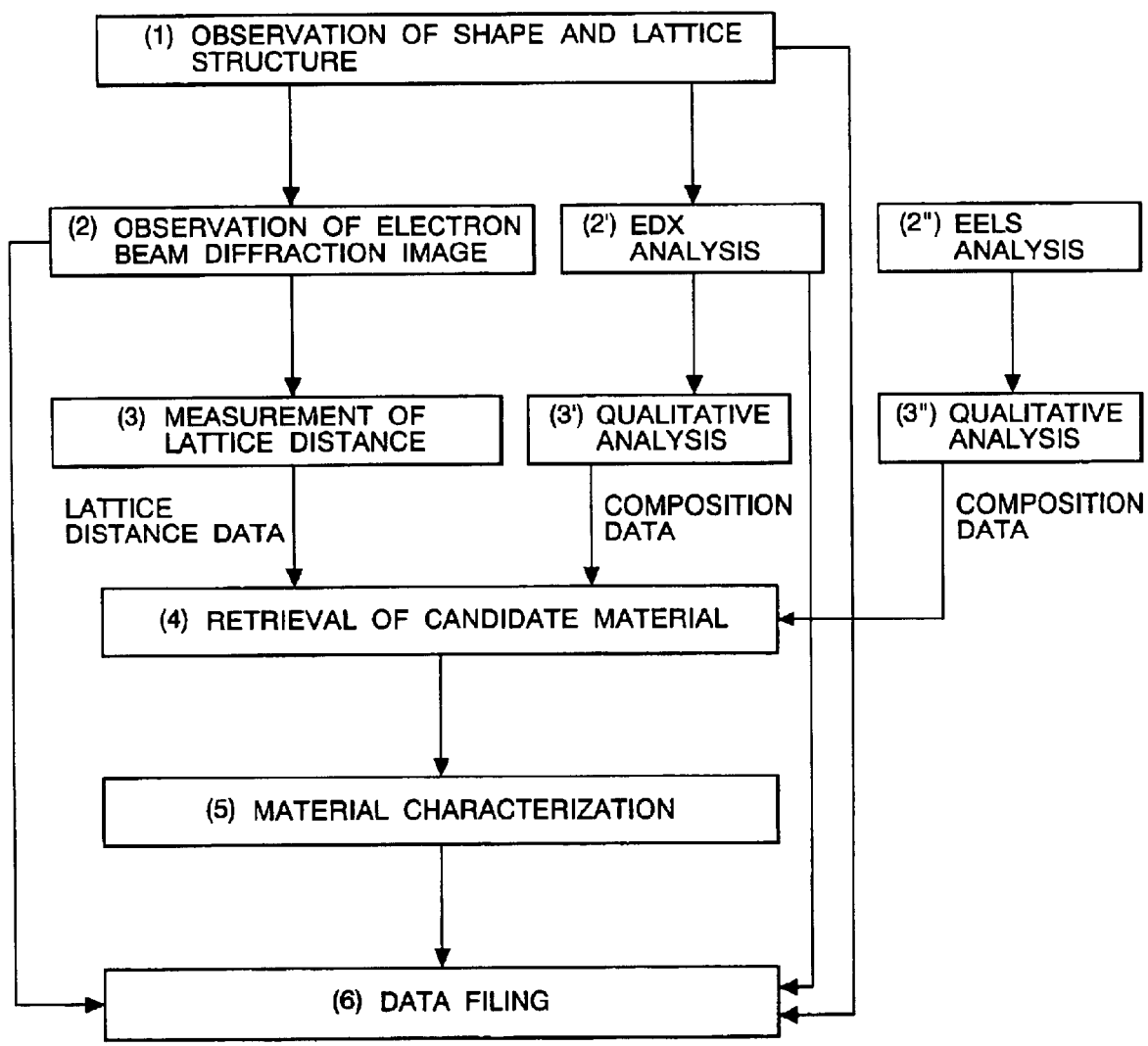
FIG. 22 is a drawing for explanation of the procedure of the material characterization section shown in FIG. 21

FIG. 22 is a drawing for explanation of the processing procedure of the material characterization system shown in FIG. 21.

The steps (1) to (3) are the same as the steps in FIG. 2. When the lattice distance data and composition data are acquired, the TV camera 10 for observation of the electron beam diffraction image is taken off from the electron beam axis, and electron beam 22, which has transmitted the specimen 15 is entered into the EELS spectroscopy 29. Since the energy that received loss by the specimen 15 depends on the material constituting the specimen, spectrum including the energy loss is acquired to obtain the composition constituting the material.

The result is inputted into the material characterization section 4.
(4) At the material characterization 4, the EELS data, the lattice distance data acquired at the step (3) and the composition data acquired at (3') are ticked off to retrieve a possible material from the retrieval data base. Or, the possible material is retrieved from the retrieval data base using only the EELS data.
(5) The material characterization result is displayed at the material characterization section 4.
(6) At the material characterization section 4, the material characterization result and a series of data of (1) to (4) are stored under the singe label.

What is claimed is:

1. A material characterization system comprising:

means for irradiating a specimen with an electron-beam by stopping down an electron beam gun;

an electron-beam scanning section for scanning the specimen with the electron-beam;

an electron detector for detecting secondary electrons emitted from the specimen upon irradiation of electron-beam or electrons transmitted through specimen;

a specimen image display section;

an elemental analysis section for analyzing an energy beam emitted by synergetic action between the electron-beam and the specimen;

an electron-beam diffraction image photography section for picking up an electron beam diffraction image formed by the specimen transmission electron-beam;

an electron-beam diffraction image analysis section for outputting information of the specimen concerning a lattice distance of a crystal obtained from the electron-beam diffraction image; and a material characterization section for characterizing the material contained in a region of electron irradiation zone of the specimen.

2. The material characterization system according to claim 1, wherein the element analysis section is an energy disperse X-ray analysis section for outputting element information by analyzing characterization X-ray emitted from the specimen upon electron beam irradiation.

3. The material characterization system according to claim 2, wherein the element analysis section has a judging section for judging whether to output the element information based on the ratio of the strength of Ka ray of characterization X-ray spectrum of each element to the strength of La ray of characterization X-ray spectrum of each element.

4. The material characterization system according to claim 1, wherein the element analysis section is an electron-beam energy loss spectroscopy section for outputting element information by analyzing energy loss spectrum of specimen transmission electron-beam.

5. The material characterization system according to claim 1, wherein a scanning image, element information, an electron-beam diffraction image and information concerning a characterized material are stored as a set of information, wherein said scanning image, element information, electron-beam diffraction image and information concerning a characterized material have been acquired by analysis of one point of the specimen.

6. The material characterization system according to claim 1, which further comprises:

an electron-beam diffraction image display section for displaying an electron-beam diffraction image photographed with the electron-beam diffraction image photography section;

a camera length adjusting lens of an electron-beam diffraction image camera; and a control section for controlling the electron-beam scanning section, wherein the control section controls the electron-beam scanning section thereby to rotate the specimen image displayed on the specimen image display section by the same angle as the rotation angle of the specimen image, the rotation angle being caused by changing of the setting of the camera length adjusting lens.

7. The material characterization system according to claim 1, which further comprises:

an electron-beam diffraction image display section for displaying an electron-beam diffraction image photographed with the electron-beam diffraction image photography section;

a camera length adjusting section of an electron-beam diffraction image camera; and a control section for controlling the electron-beam diffraction display section;

wherein the control section controls the electron-beam scanning section thereby to rotate the image displayed on the specimen image display section in the reverse direction by the same angle as the rotation angle of the specimen image, the rotation angle being caused by changing of the setting of the camera length adjusting lens.

8. The material characterization system according to claim 1, wherein the electron-beam image analysis section comprises:

means for making a short axis strength profile accumulating pixel strength in the lengthwise direction in each of the short lengths of a square region set so as to embrace a main spot in the center and at least two spots which are set for the electron-beam diffraction image of a spot form displayed on the electron-beam diffraction display section;

means for making a long axis strength profile accumulating pixel strength in the short length direction in each of lengthwise sides of the square region, wherein said lengthwise sides are the long lengths of the square region;

means for rotating the square region around the center thereof; and means for calculating the lattice distance of a crystal from a distance between peaks of the profiles measured at rotating positions of the square region when the profile in the short length direction is the maximum.

9. The material characterization system according to claim 1, wherein the electron-beam diffraction analysis section comprises:

means for making a short length profile accumulating pixel strength in the lengthwise direction in each of the short lengths of a square region set so as to embrace at least two spots which are set for the electron-beam diffraction image of a spot form displayed on the electron-beam diffraction display section;

means for making a long axis strength profile accumulating pixel strength in the short length direction in each of lengthwise sides of the square region, wherein said lengthwise sides are the long lengths of the square region; and means for calculating the lattice distance of a crystal based on a distance between the two spots, the distance being calculated from the peak position of the short axis strength profile and the peak position of the long axis peak profile.

10. The material characterization system according to claim 1, wherein the electron-beam diffraction image analysis section comprises:

means for acquiring a pixel distribution strength at each of first and second regions which are so set as to embrace two spots of electron beam images displayed on the electron-beam diffraction display section; and means for calculating a lattice distance based on the distance between the spots calculated as the distance between the peak positions of each of the pixel strength distributions.

11. The material characterization system according to claim 1, wherein the electron-beam image analysis section comprises:

means for acquiring pixel strength distributions in a region so set as to embrace a main spot displayed on the electron-beam diffraction image display section with respect to the electron-beam diffraction image of a concentric circle where the main spot is the center;

means for acquiring a peak position of the pixel strength distribution;

means for acquiring a strength profile on the straight line intersecting the concentric circle via the peak position;

means for acquiring the peak position of the strength profile; and means for calculating the lattice distance of a crystal based on the peak distance on the straight line.

12. The material characterization system according to claims 8 to 11, wherein the peak of the strength profile is acquired by fitting the strength profile to a normal distribution line or a parabola line.

13. A material characterization system, comprising:

means for irradiating a specimen with an electron-beam by stopping down the electron-beam;

an X-ray detector for detecting characterization X-ray emitted from the specimen irradiated with the electron-beam;

an energy dispersive X-ray analysis section for outputting elemental information by analyzing the characterization X-ray detected by the X-ray detector; an a judging section for judging whether the characterization X-ray stems from the element present in the irradiated region or not, based on the strength ratio of the Ka and La lines of characterization X-ray identified as ones of an element by the energy dispersive X-ray analysis section, wherein the strength ratio is determined as a ratio of the respective signal strengths of the La and Ka lines of characterization, otherwise expressed as ($I_L/I_K$).

* * * * *